US008252281B2

(12) United States Patent
Levy et al.

(10) Patent No.: US 8,252,281 B2
(45) Date of Patent: Aug. 28, 2012

(54) METHODS FOR THE TREATMENT OF SEPSIS AND SEPSIS-ASSOCIATED CARDIAC DYSFUNCTION

(75) Inventors: Richard J. Levy, New York City, NY (US); Clifford S. Deutschman, Narberth, PA (US)

(73) Assignees: The Children's Hospital of Philadelphia, Philadelphia, PA (US); The Trustee of the University of Pennsylvania, Philadelphia, PA (US)

( * ) Notice: Subject to any disclaimer, the term of this patent is extended or adjusted under 35 U.S.C. 154(b) by 975 days.

(21) Appl. No.: 11/816,230

(22) PCT Filed: Feb. 14, 2006

(86) PCT No.: PCT/US2006/005109
§ 371 (c)(1),
(2), (4) Date: Jul. 25, 2008

(87) PCT Pub. No.: WO2006/088832
PCT Pub. Date: Aug. 24, 2006

(65) Prior Publication Data
US 2009/0024105 A1 Jan. 22, 2009

Related U.S. Application Data

(60) Provisional application No. 60/652,612, filed on Feb. 14, 2005, provisional application No. 60/702,647, filed on Jul. 26, 2005.

(51) Int. Cl.
*A61K 38/43* (2006.01)
*C12P 21/06* (2006.01)
*C07K 1/00* (2006.01)
(52) U.S. Cl. ......................... 424/94.1; 435/69.1; 435/29
(58) Field of Classification Search .................. 424/94.1; 435/69.1, 29
See application file for complete search history.

(56) References Cited

U.S. PATENT DOCUMENTS
5,439,883 A 8/1995 Karsanov et al.

OTHER PUBLICATIONS

Tessier et al. Impairment of glucose metabolism in hearts from rats treated with endotoxin. 2003. Cardiovascular Research 60: 119-130.*
Mootha et al. A reversible component of mitochondrial respiratory dysfunction in apoptosis can be rescued by exogenous cytochrome c. 2001. EMBO 20(4) 661-671.*
Chen et al. Heat Shock Pretreatment Prevents Cardiac Mitochondrial Dysfunction During Sepsis. 2003. SHOCK 20(3) 274-279.*
Proger et al. Some observations of the effect of injected cytochrome C in animals. 1945. Journal of Clinical Investigations. 24(6) 864-868.*
Levy, Richard J., et al. "Competitive and Noncompetitive Inhibition of Myocardial Cytochrome C Oxidase in Sepsis." Shock, vol. 21., No. 2. 2004. pp. 110-114.
Levy, Richard J., et al. "Evidence of Myocardial Hibernation in the Septic Heart." Continuing Medical Education, vol. 33. No. 12. 2005. pp. 2752-2756.
Levy, Richard J. "Mitochondrial Dysfunction, Bioenergetic Impairment, and Metabolic Down-Regulation in Sepsis." Shock, vol. 28., No. 1. 2007. pp. 24-28.
Slepneva, L.V., et al. "Effect of Parenteral Administration of Exogenous Cytochrome C on Cytochrome Content in the Liver of Rabbits with Chronic Carbon Tetrachloride Poisoning." [Abstract] Bulletin of Experimental Biology and Medicine: Translated from Byulleten Eksperimental'noi Biologii i Meditsiny, vol. 82, No. 10. Oct. 1976. pp. 1215-1216.
Slepneva, L.V., et al. "Effect of Parenteral Administration of Exogenous Cytochrome C on Cytochrome Content in the Liver of Rabbits with Chronic Carbon Tetrachloride Poisoning." Bulletin of Experimental Biology and Medicine: Translated from Byulleten Eksperimental'noi Biologii i Meditsiny, vol. 82, No. 10. Oct. 1976. pp. 1215-1216.

* cited by examiner

*Primary Examiner* — Karen Cochrane Carlson
*Assistant Examiner* — Natalie Moss
(74) *Attorney, Agent, or Firm* — Dann Dorfman Herrell & Skillman; Kathleen D. Rigaut

(57) ABSTRACT

Methods for the treatment of sepsis related cardiac dysfunction are disclosed.

10 Claims, 24 Drawing Sheets
(3 of 24 Drawing Sheet(s) Filed in Color)

Baseline    Sham    2CLP

METHODS FOR THE TREATMENT OF SEPSIS AND SEPSIS-ASSOCIATED CARDIAC DYSFUNCTION

PRIORITY CLAIM

The present application is a §371 application of PCT/US06/05109 filed Feb. 14, 2006 which in turn claims priority to US Provisional Applications 60/652,612 and 60/702,647 filed Feb. 14, 2005 and Jul. 26, 2005 respectively. The entire disclosure of each of the above identified applications is incorporated by reference herein.

Pursuant to 35 U.S.C. Section 202(c), it is acknowledged that the United States Government has certain rights in the invention described herein, which was made in part with funds from the National Institutes of Health Grant Nos. 5K08GMO74117-02 and RO1 GM59930.

FIELD OF THE INVENTION

The present invention relates to the fields of cardiology and pharmacology. More specifically, the invention provides methods for the treatment of sepsis and sepsis-associated cardiac dysfunction.

BACKGROUND OF THE INVENTION

Several publications and patent documents are cited throughout the specification in order to describe the state of the art to which this invention pertains. Each of these citations is incorporated herein by reference as though set forth in full.

Sepsis is the most common cause of death in intensive care units worldwide. The basic pathophysiologic defect in sepsis, causing functional abnormalities in many organ systems, remains elusive. Cardiovascular dysfunction often occurs in patients with sepsis and can present in two ways. After adequate volume resuscitation, patients in hyperdynamic or warm shock are peripherally vasodilated with a high cardiac output. Patients in a hypodynamic state (cold shock) present with increased vascular tone and low cardiac output (Kumar et al. (2000) Crit Care Clin. 16:251-287). Adults with sepsis often present in hyperdynamic shock, whereas pediatric patients can present with warm or cold shock (Ceneviva et al. (1998) Pediatrics 102:e19). Meningococcal sepsis can lead to hypodynamic shock in adults and children (Ceneviva et al., supra).

Despite an increase in cardiac output during the hyperdynamic phase of sepsis, studies indicate that the myocardium is dysfunctional. Both right and left ventricles can dilate, contractile function may decrease, and ventricular compliance is reduced (Kumar et al., supra). Additional work has demonstrated severe depression of ejection fraction in some patients with sepsis despite normal or elevated cardiac index (Parker et al., (1984) Ann Int Med 100:483-490). This dysfunction peaks within a few days of the onset of sepsis and resolves within 7 to 10 days in surviving patients (Kumar et al., supra).

Although myocardial dysfunction in sepsis has been the focus of many investigations, its etiology remains unclear. Given the significant link between sepsis and mortality, it is clear that a need exists for improved methodologies for the treatment and resolution of sepsis.

SUMMARY OF THE INVENTION

In accordance with the present invention, methods for the treatment of sepsis and sepsis-associated cardiac dysfunction in a patient in need thereof comprising the administration of an effective amount of cytochrome c are provided. In a particular embodiment, cytochrome c is administered intravenously. The method of the invention may also comprise combined administration of cytochrome c and ascorbate, where the ascorbate is provided in an amount effective to reduce cytochrome c.

In accordance with another aspect of the instant invention, the above methods are used for the treatment of sepsis associated with a condition which includes, but is not limited to, systemic inflammatory response syndrome (SIRS) and multiple organ dysfunction syndrome (MODS). Additionally, the methods can be used to treat cardiac dysfunction and organ dysfunction associated with conditions such as burns, trauma, hemorrhage, cardiopulmonary bypass, hypoxia and ischemia, cardiomyopathies, inborn errors of metabolism, smoke inhalation, carbon monoxide poisoning, induction of stasis or hibernation and mitochondriopathies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 16A provides representative positron emission tomography scans following 18-FDG injection. Images are transverse sections of the thorax with the mouse supine. The more dense, circular structures within the thorax represent glucose uptake in the heart. Baseline, nonoperated control; sham, sham-operated control; 2CLP, septic mouse that underwent cecal ligation and double puncture. FIG. 16B is a graphical representative of the relative densities of myocardial 18-FDG uptake. Black bar, baseline (unoperated control); white bar, sham operation; gray bar, 2CLP. Values represent mean plus the SD of three study animals in each group. Baseline density was set arbitrarily at unity. *$p<0.001$ vs. baseline and sham. FIG. 16C provides representative immunoblots of the myocardial specific glucose transporters, GLUT4 and GLUT1. Baseline, nonoperated control; S, sham operated control; 2CLP, septic mouse that underwent cecal ligation and double puncture. FIG. 16D provides graphical representative of the relative steady-state densities of GLUT4 (left) and GLUT1 (right). Values represent mean plus the SD. Baseline density was set arbitrarily at unity. *$p<0.02$ vs. baseline and sham; †$p<0.05$ vs. baseline and 2CLP; ‡$p<0.05$ vs. baseline and sham. n=3. FIG. 16E provides representative hematoxylin and eosin and periodic acid-Schiff stains of myocardium from nonoperated controls (baseline), sham-operated controls (sham), and septic mice (2CLP). Magenta staining (arrows) between cardiomyocytes and in the perinuclear region illustrates increased glycogen deposition in septic myocardium.

FIG. 17A provides representative single photon emission computed tomography scan images following (99 m)Tc sestamibi injection. Images are short axis sections through the left ventricle. Baseline, nonoperated control; sham, sham-operated control; 2CLP, septic mouse that underwent cecal ligation and double puncture. FIG. 17B provides graphical representative of the relative densities of myocardial (99 m)Tc sestamibi. Black bar, baseline (nonoperated control); white bar, sham operation; gray bar, 2CLP. Values represent the mean plus the SD. Baseline density was set arbitrarily at unity. n=3.

DETAILED DESCRIPTION OF THE INVENTION

Figure 1:
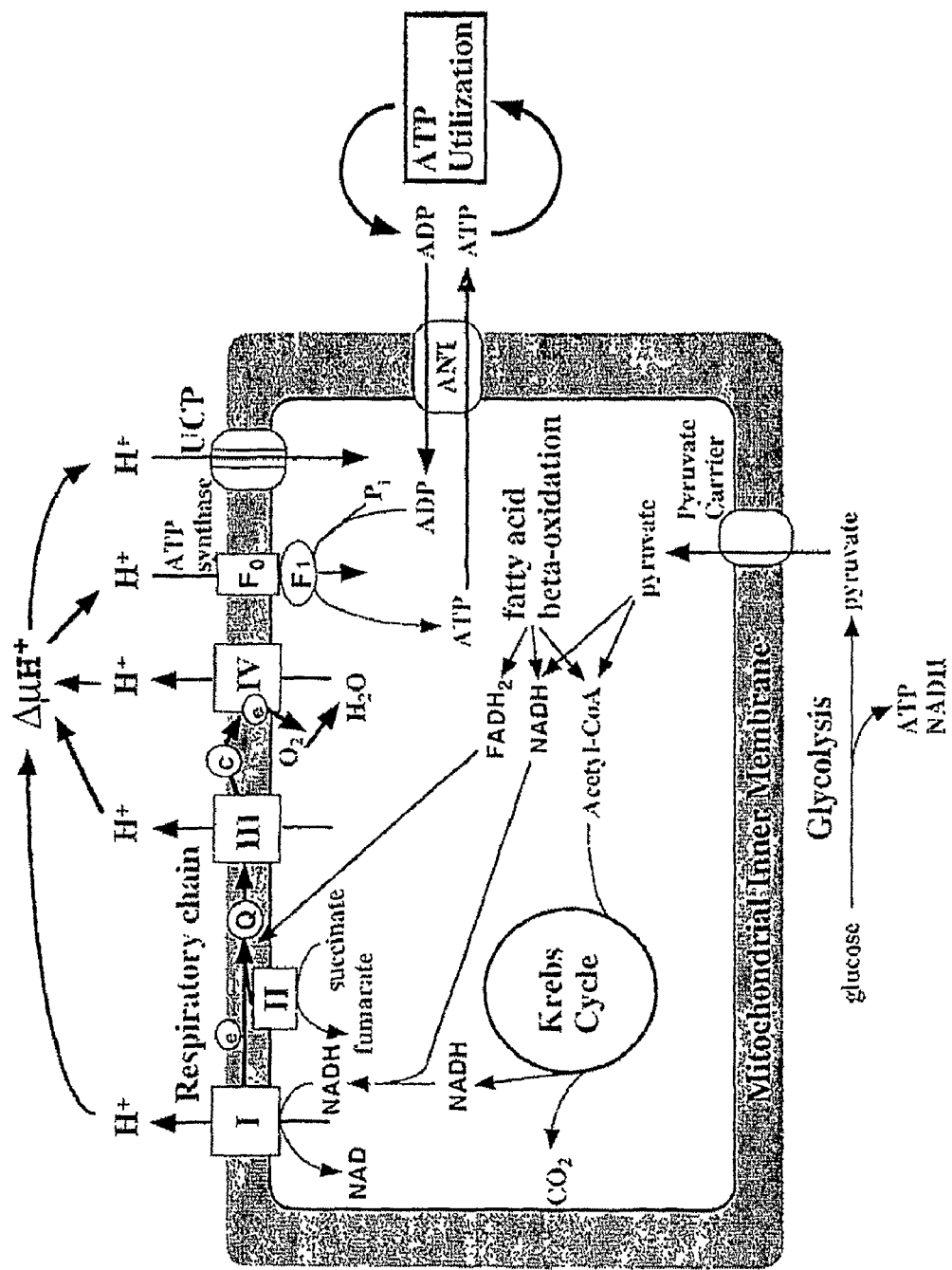
FIG. 1 provides a schematic diagram of oxidative phosphorylation.
Figure 2A:
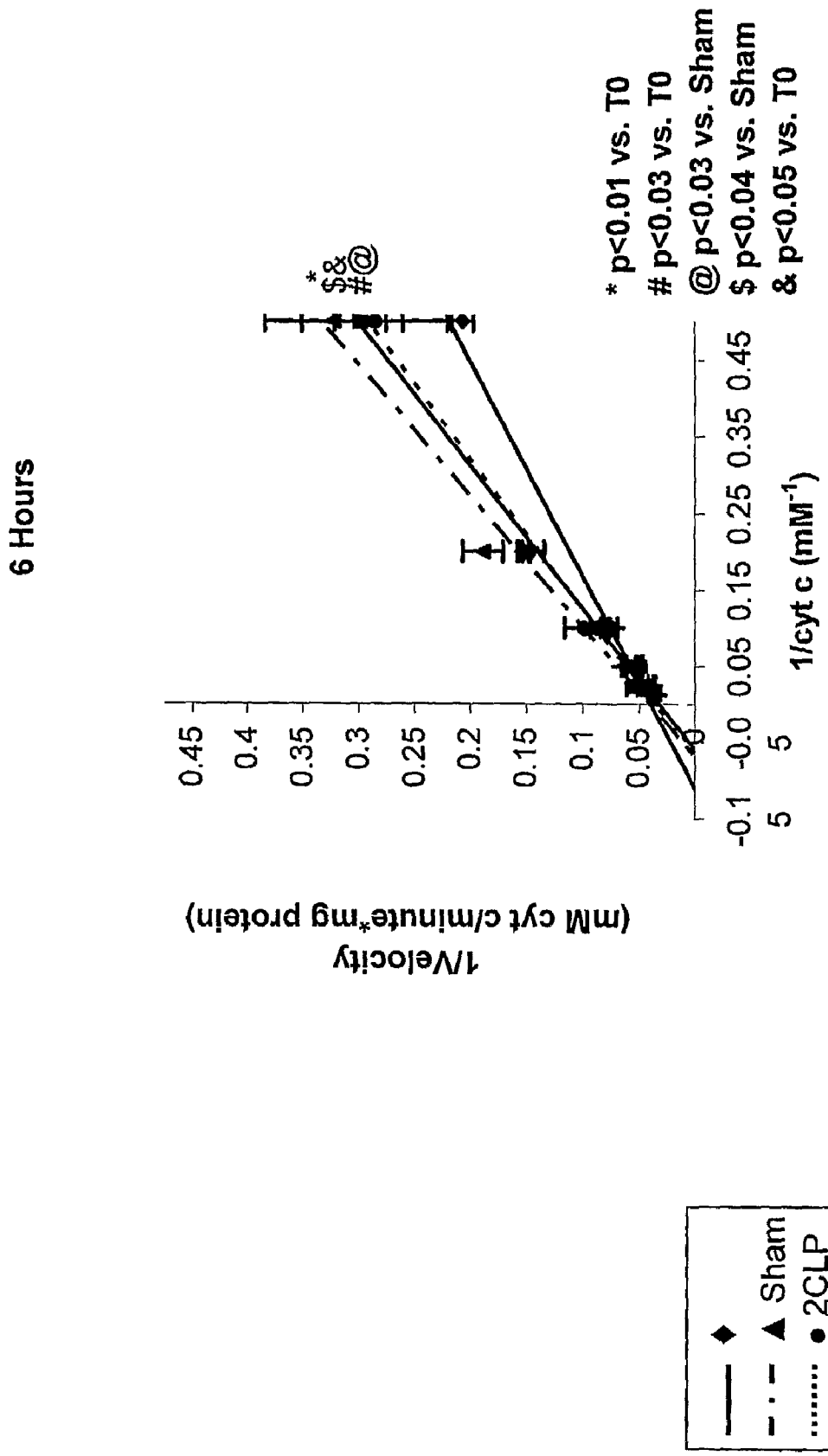
FIGS. 2A-2D provide Lineweaver-Burk plots of myocardial cytochrome c oxidase kinetic activity. The plots represent kinetic activity at 6, 16, 24, and 48 hours post CLP (FIGS. 2A-2D, respectively). CLP represents mild, survivable sepsis and 2CLP represents severe, lethal sepsis. The time zero, non-operative control (♦) in each plot represents baseline kinetics. Means are represented +/− standard deviation (SD), n=3 at each time point. Linear regression of each set of points was drawn and extended to the x-axis to determine 1/Vmax (y-intercept) and −1/Km (x-intercept) (Levy R J et al., Shock. 2004, 21:110-114).
Figure 2B:
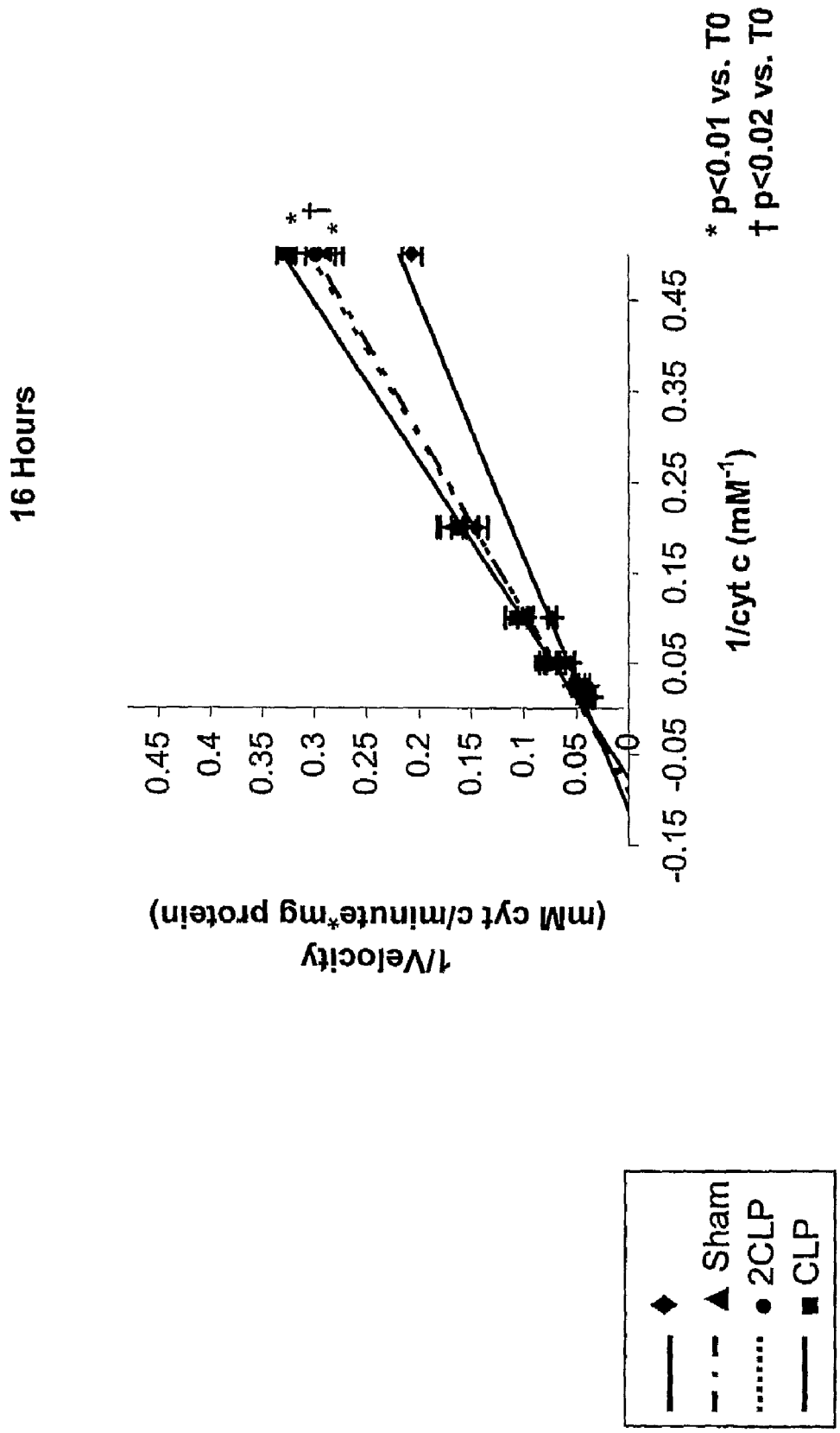
Figure 2C:
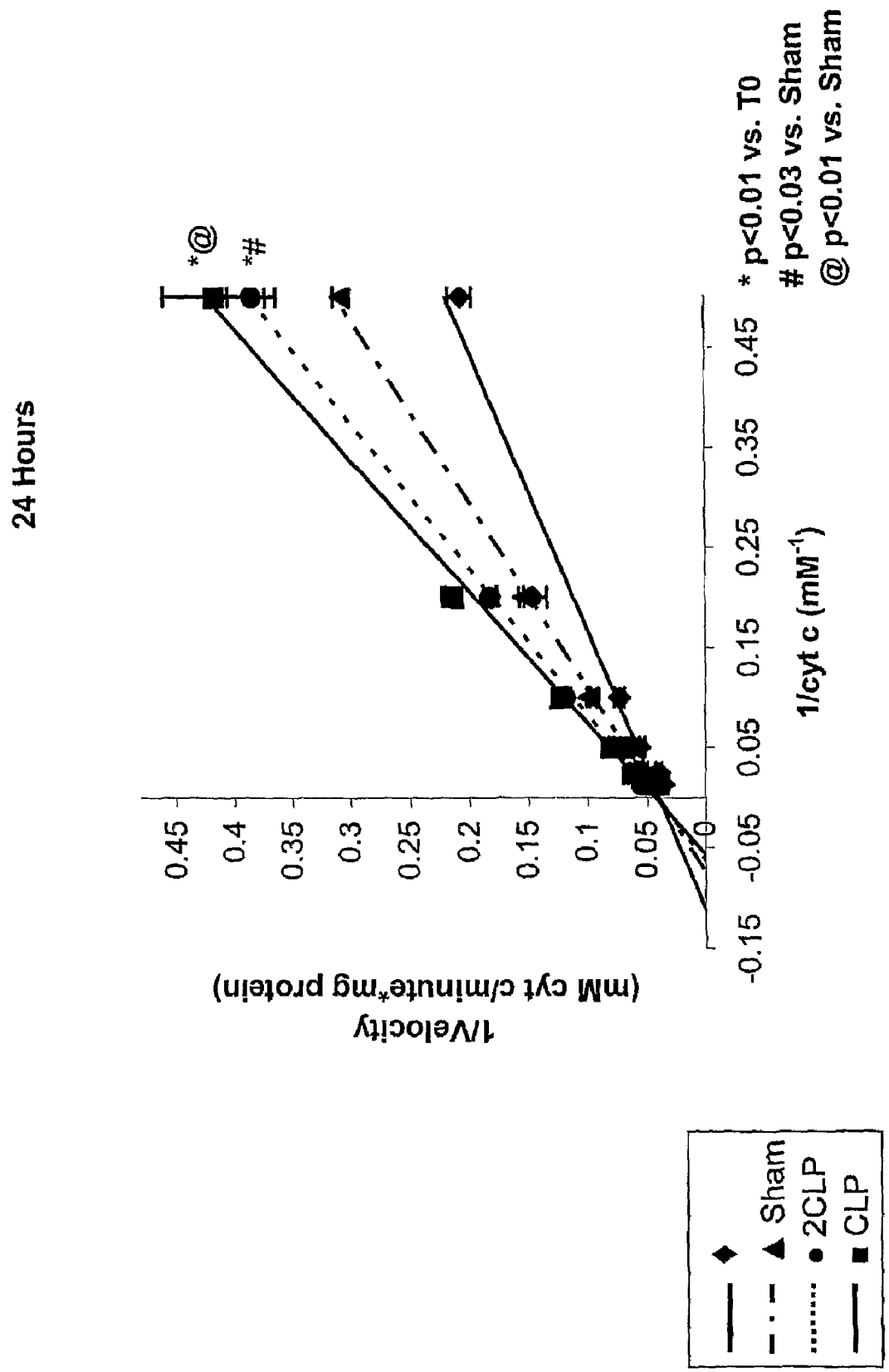
Figure 2D:
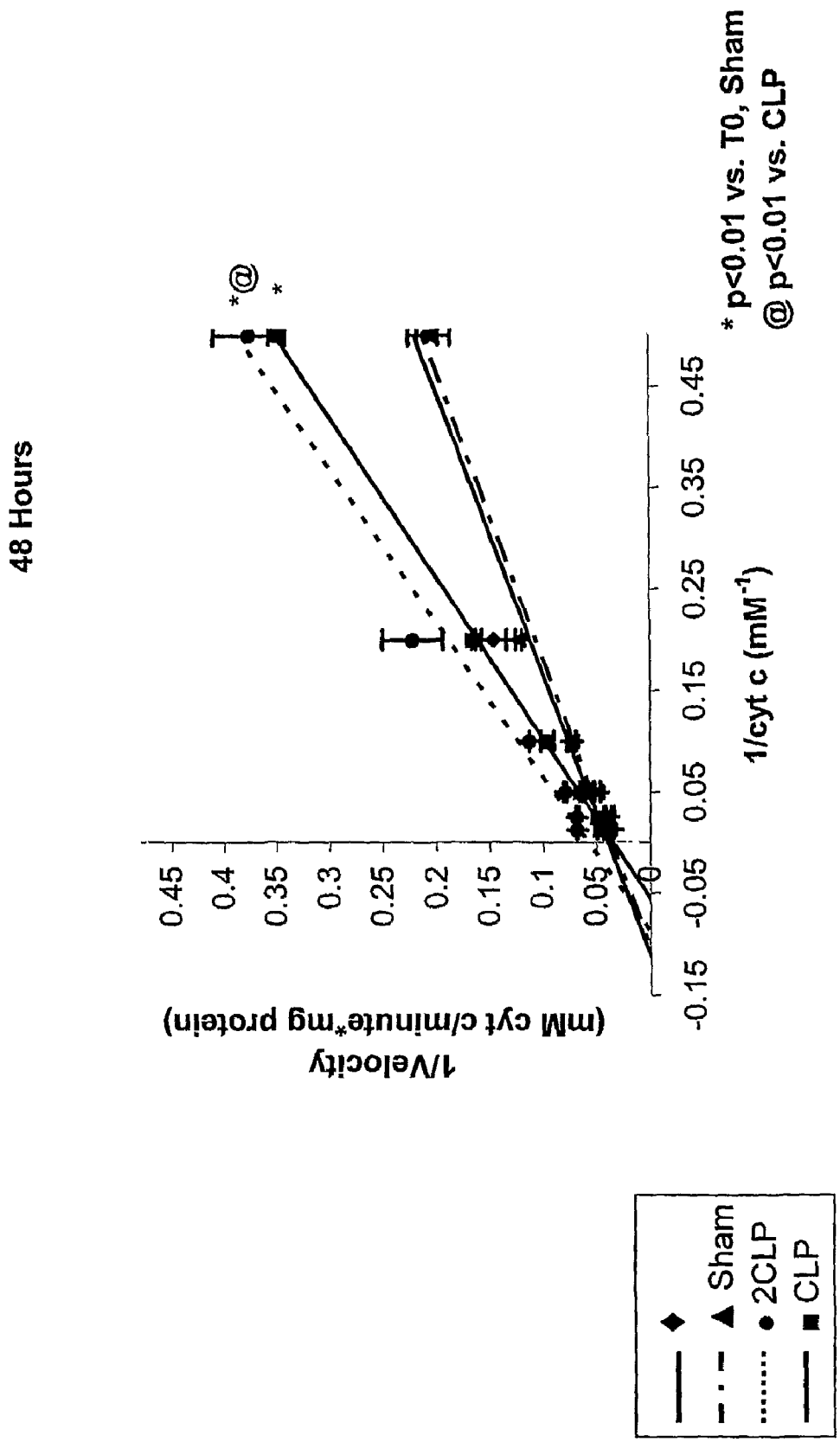

Sepsis is the body's overwhelming response to severe infection and often involves depression of heart function. In earlier studies, the role of the enzyme cytochrome c oxidase was evaluated in the septic heart. Cytochrome oxidase is an enzyme in mitochondria that utilizes oxygen to make cellular energy. It has been demonstrated that myocardial cytochrome oxidase is reversibly inhibited early in sepsis and becomes irreversibly inhibited later when mortality is high. During reversible (competitive) inhibition, the velocity of enzyme activity can be increased by increasing substrate availability. The substrate for cytochrome oxidase is cytochrome c. In the septic heart, cytochrome c availability decreases. Thus, in accordance with the present invention, methods for the administration of cytochrome c to the septic patient are provided. While not being bound by theory, administration of cytochrome c should be effective to increase the velocity of reversibly inhibited cytochrome oxidase during sepsis by increasing substrate availability. This will restore the energy producing potential of the cell and prevent the progression to irreversible inhibition of cytochrome oxidase. At the organ level, the effect of restored bioenergetics should result in preserved cardiac function. Cytochrome c is commercially available and can be purchased from Sigma Aldrich (St. Louis, Mo.).

The intravenous administration of cytochrome c may also be therapeutically beneficial to other organ systems besides the heart and improve survival during sepsis. In another aspect, cytochrome c may be administered to reverse any process associated with cytochrome oxidase inhibition.

The present invention also encompasses the co-administration of at least one other agent that improves cardiac dysfunction (e.g. ascorbic acid) with cytochrome c for the treatment of sepsis.

Definitions:

The term "sepsis", as used herein refers to the systemic inflammatory response associated with infection. The "systemic inflammatory response" is the body's overwhelming response to a noxious stimulus. The current definition is characterized by the following non-specific changes in the adult human body:

fast heart rate (tachycardia, heart rate >90 beats per minute)
low blood pressure (systolic <90 mmHg or MAP <65 mmHg)
low or high body temperature (<36 or >38° C.)
high respiratory rate (>20 breaths per minute)
low or high white blood cell count (<4 or >12 billion cells/liter).

SIRS or the systemic inflammatory response syndrome can be caused by burns, trauma (including surgery), hemorrhage, pancreatitis, and/or infection.

When an identified infectious pathogen causes the inflammatory response, the resultant inflamed state is referred to as sepsis. Infectious agents which can cause sepsis include bacteria, viruses, fungi, and parasites.

"Hypoxemia" refers to inadequate levels of oxygen in the blood or circulation.

"Hypoxia" refers to inadequate levels of oxygen at the tissue or cellular level.

Ischemia is defined as inadequate oxygen delivery to the tissues.

Oxygen delivery is determined by oxygen content and cardiac output. Therefore ischemia and hypoxia are closely related. Sepsis may also be related to ischemia and hypoxia. Sepsis causes a defect at the mitochondrial level such that cells cannot use oxygen for energy production. Although the impact on the cell may be similar to ischemia and hypoxia, the etiology is different. During sepsis, oxygen levels at the tissue and cellular level are normal or elevated and oxygen delivery is also maintained or increased. Therefore ischemia and hypoxia do not contribute to the pathogenesis of sepsis. However, the cell may become "functionally hypoxic" during sepsis, because even though there is adequate oxygen available, the cell cannot use the oxygen for aerobic oxidative phosphorylation. This inability to use molecular oxygen for energy production during sepsis has been termed "cytopathic hypoxia".

A number of disease processes are related to sepsis in that they may lead to abnormalities in cytochrome oxidase function and inhibition. Such defects in enzyme function may be amenable to intravenous cytochrome c therapy. These related disorders include:

SIRS
MODS (multiple organ dysfunction syndrome)
Trauma (including surgery)
Hemorrhage
Burns
Smoke inhalation (carbon monoxide poisoning)
Cyanide toxicity
Cardiopulmonary bypass
Ischemia
Hypoxia
Cardiomyopathy
Mitochondrial disorders (inherited and acquired)
Induced stasis, suspended animation, or hibernation induced by exposure to gases such as hydrogen sulfide or carbon monoxide. See for example US Patent Applications 20050053912 and 20050136125, which are incorporated by reference herein.

The term "treat" as used herein refers to any type of treatment that imparts a benefit to a patient afflicted with a disease, including improvement in the condition of the patient (e.g., in one or more symptoms), delay in the progression of the condition, etc.

The phrase "effective amount" refers to that amount of therapeutic agent which results in an improvement in the patient's condition.

The term "administration" as used herein refers to delivery of at least one therapeutic agent to a patient. The pharmaceutical compositions of the invention may be prepared in various forms for administration, including tablets, caplets, pills, or dragees, or can be filled in suitable containers, such as capsules, or, in the case of suspensions, filled into bottles.

The terms "stasis, hibernation and/or suspended animation" are used interchangeably herein and refer to those conditions described in US Patent Application 20050136125. Inducing stasis in biological matter or an organism means that the matter or organism is alive but is characterized in by one or more of the following: at least a two-fold reduction in the rate or amount of carbon dioxide production by the biological matter; at least a two-fold reduction in the rate or amount of oxygen consumption by the biological matter; and at least a 10% decrease in movement or motility (applies only to cells or tissue that move, such as sperm cells or a heart or a limb, or when stasis is induced in the entire organism) (collectively referred to as "cellular respiration indicators"). As used herein, stasis or hibernation is temporary and/or reversible, meaning that the biological matter no longer exhibits the characteristics of stasis at some later point in time. Biological matter as used above, refers to any living biological material including without limitation, cells, tissues, organs, and/or organisms.

An organism in need of stasis is an organism in which stasis of all or part of the organism may yield direct or indirect physiological benefits. For example, a patient at risk for hemorrhagic shock may be considered in need of stasis, or a patient who will undergo coronary artery bypass surgery may benefit from protecting the heart from ischemia/reperfusion injury. Other applications are discussed throughout the application. In some cases, an organism is identified or determined to be in need of stasis based on one or more tests, screens, or evaluations that indicate a condition or disease, or the risk of a condition or disease that can be prevented or treated by undergoing stasis. Alternatively, the taking of a patient medical or family medical history (patient interview) may yield information that an organism is in need of stasis. Surprisingly, it has been discovered that administration of cytochrome c as disclosed herein is effective to reverse stasis or hibernation.

As used herein, "a pharmaceutically acceptable carrier medium" includes any and all solvents, diluents, other liquid vehicles, dispersion or suspension aids, surface active ingredients, preservatives, solid binders, lubricants, and the like, as suited to the particular dosage form desired. *Remington's Pharmaceutical Sciences*, Fifteenth Edition, E. W. Martin (Mack Publishing Co., Easton Pa. 1975) discloses various vehicles or carriers used in formulating pharmaceutical compositions and known techniques for the preparation thereof. Except insofar as any conventional carrier medium is incompatible with the compounds of the invention, (such as by producing any undesirable biological effect or otherwise interacting in a deleterious manner with any other component(s) of the pharmaceutical composition), its use is within the scope of the invention.

In the pharmaceutical compositions of the invention, the active agents may be present in an amount of at least about 0.1% and not more than about 95% by weight, based on the total weight of the compositions, including carrier medium and auxiliary agent(s). Preferably, the proportion of active agent varies between about 1% and about 75% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The compositions described herein may be formulated in dosage unit form for ease of administration and uniformity of dosage. "Dosage unit form" as used herein refers to a physically discrete unit of the composition for the patient to be treated. Each dosage should contain the quantity of active material calculated to produce the desired therapeutic effect either as such, or in association with the selected pharmaceutical carrier medium. The compositions of the invention may be administered orally, parenterally, by intramuscular injection, intraperitoneal injection, intravenous infusion, or the like. Intravenous administration is particularly preferred. The compositions of the invention are typically administered by intravenous infusions of varying duration, with infusions of 1 hour to 24 hours being preferred.

The compositions may be administered as often as necessary to obtain the desired therapeutic effect. In a preferred embodiment of the present invention, the cytochrome c is administered to the septic patient as a single intravenous bolus injection.

The following examples are provided to illustrate certain embodiments of the invention. They are not intended to limit the invention in any way.

EXAMPLE 1

Material and Methods

Mice were obtained from Charles River Laboratories (Wilmington, Mass.). Cecal ligation and puncture (CLP) (a well accepted model of sepsis) or sham operation under general anesthesia was performed (Levy R J, et al. Shock 21:110-114, 2004). After induction of anesthesia with up to 2% isoflurane while spontaneously breathing, the abdomen was shaved with electric clippers. The abdomen was then sterilized with betadine solution followed by rinsing with 70% alcohol. A 1 cm vertical incision was made with sterile scissors. The muscle layer was then incised along the linea alba. Using a sterile q-tip, the cecum was identified and mobilized out of the peritoneum onto parafilm. During sham operation, the cecum is returned to the peritoneum and the incision sutured closed. For CLP, a 4-0 silk ligature is placed around the cecum just distal to the ileocecal valve. Three knots are made and the ends cut. The antimesenteric border of the cecum is identified and punctured twice with a 23-guage needle. Fecal material is then expressed and the cecum returned to the abdominal cavity. Using 4-0 silk, the incision is sutured closed in two layers. In both sham and CLP mice, 50 cc/kg of saline (1 cc) is subcutaneously injected into the scruff of the neck using a tuberculin syringe while the mice are still anesthetized. Animals are allowed to recover in a warmed separate container and are returned to their containment box when awake. Animals are allowed to feed and drink ad lib. At 24 hours post procedure, mice are anesthetized with up to 2% isoflurane. Animals randomized to receive cytochrome c are then injected with 800 µg (0.2 cc) of reduced cytochrome c (see below) via the tail vein. The other mice are injected with 0.2 cc of saline via tail vein (sham injection). Mice are then allowed to awaken and recover in a warmed containment box. For experiments designed to evaluate the 24 hour time point, mice are injected with 150 mg/kg of intraperitoneal pentobarbital 30 minutes following iv cytochrome c injection. Following apnea and unresponsiveness, the heart is harvested for further study via a median sternotomy. For experiments designed to evaluate the 48 hour time point, mice receive 50 cc/kg of subcutaneous saline following tail vein injection while still under anesthesia. They are allowed to recover in a warmed containment box and have unrestricted access to food and water. At 48 hours post procedure they are euthanized with 150 mg/kg of intraperitoneal pentobarbital. Following apnea and unresponsiveness, the heart is harvested for further study via a median sternotomy.

Prior to administration, cytochrome c is reduced in 10 mM dibasic sodium phosphate (pH 7.0) and excess ascorbate at 4° C. overnight. Final concentration of reduced cytochrome c is determined by spectrophotometric absorbance at 550 nm using 21.1 $mM^{-1} cm^{-1}$ as the extinction coefficient of ferrocytochrome c (Levy R J, et al. Shock 21: 110-114, 2004). Addition of 50 mg cytochrome c to 10 mL sodium phosphate yields approximately 0.4 mM cytochrome c (800 µg/0.2 µl).

Results

In accordance with the present invention, it has been discovered that administration of cytochrome c is effective to ameliorate the cardiac dysfunction associated with sepsis. Sepsis, the Systemic Inflammatory Response Syndrome (SIRS), and the Multiple Organ Dysfunction Syndrome (MODS) are the most common causes of death in surgical intensive care units. Cardiac dysfunction is an important but poorly understood characteristic of these syndromes. The time course and progression of myocardial depression, involving both systolic and diastolic abnormalities, have been well described in humans and animals. Sepsis results in depressed myocardial contractility. Adequate volume resuscitation and increased preload increase end-diastolic volume leading to biventricular dilatation. This enables stroke volume and cardiac output to be maintained in the face of reduced ejection fraction and myocardial dysfunction. Ultimately, however, reduced diastolic relaxation can lead to inability of the heart to dilate and cardiac output can decrease. This inability of the heart to dilate often leads to death.

Although a number of mediators and pathways have been implicated in the pathogenesis of myocardial depression in sepsis, a unifying cause has yet to be found. One explanation for the host of abnormalities found in sepsis is an interruption in oxidative phosphorylation resulting in an inability of the cell to use molecular oxygen for energy production. This defect occurs despite adequate oxygen availability at the cellular level. As a result, there is a decrease in the bioenergy available for contraction and other important cellular functions. This alteration may explain the underlying etiology of sepsis-associated cardiac dysfunction. In addition, impaired oxidative phosphorylation in other organ systems could lead to multiple organ failure in sepsis.

In the setting of sepsis (with the hypothesis that there is an inability to use oxygen), the enzyme complex most intriguing to study is complex IV, cytochrome oxidase, which is the terminal oxidase in the electron transport chain (FIG. 1). Cytochrome oxidase uses electrons donated by cytochrome c (which arises from complex III) to reduce molecular oxygen to water. The consumption of oxygen in this process is closely linked to proton pumping across the inner mitochondrial membrane. Complex V then uses the trans-membrane proton gradient for ATP generation.

Alterations in cytochrome oxidase activity and its redox state have been described previously in a murine model of sepsis (cecal ligation and puncture, CLP). In related work, cytochrome oxidase activity and redox state have been reported to be decreased in skeletal muscle, cardiomyocytes, and in macrophages exposed to endotoxin. Thus, it is logical that a global hypothesis to explain sepsis-associated myocardial depression includes an alteration in cytochrome oxidase activity.

Inhibition of myocardial cytochrome oxidase following CLP has been reported. Specifically, early competitive inhibition of myocardial cytochrome oxidase, followed by CLP progressing to irreversible inhibition has been demonstrated, during the hypodynamic phase of sepsis (see FIG. 2). Competitive cytochrome oxidase inhibition progressed until 24 hours post CLP. At 48 hours, Vmax decreased and the inhibition became non-competitive.

Figure 3:
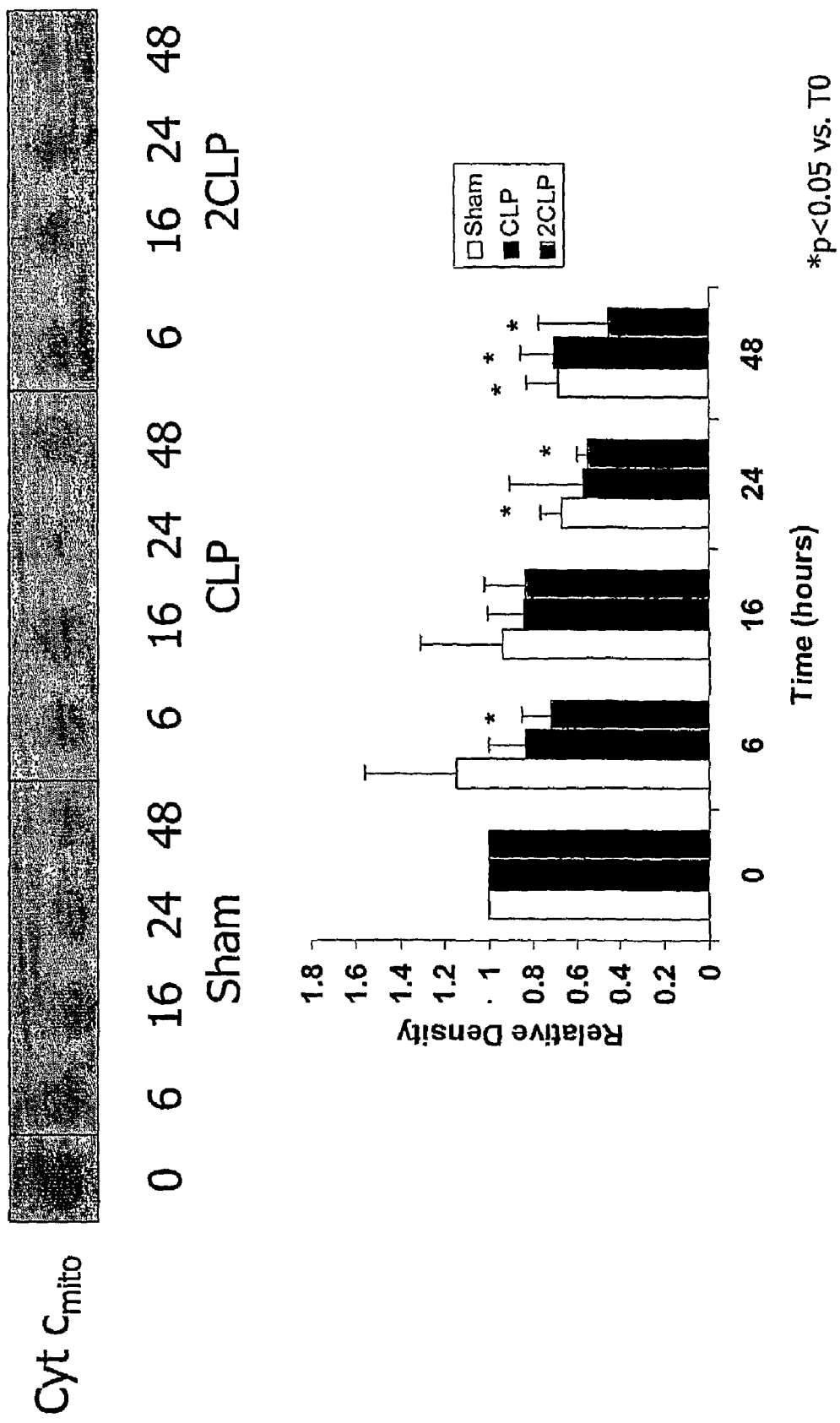
FIG. 3 provides a representative Western blot of mitochondrial cytochrome c levels with relative density graphically depicted. Isolated mitochondria at 6, 16, 24, or 48 hours following procedure were evaluated. 0 is healthy non-operative control, sham is operative control, CLP is mild sepsis, 2CLP is severe sepsis. N=3 per group per time point. Means +/−SD are provided.

Notably, at 24 hours, there is a switch from the early, hyperdynamic phase to the late, hypodynamic phase of sepsis. Furthermore, after 24 hours, CLP induced mortality increases substantially, becoming 75% lethal at 48 hours and 90% lethal by 72 hours. In addition, mitochondrial cytochrome c (substrate) levels in cardiomyocytes decrease significantly 24 hours post CLP (FIG. 3). Reduced substrate concentration during enzyme inhibition is known to reduce enzyme activity. During competitive inhibition, affinity for substrate (Km) and enzyme activity are reduced while maximum velocity (Vmax) of the enzyme is maintained by increased substrate concentrations. During non-competitive inhibition, enzyme activity and Vmax are diminished irrespective of substrate concentration.

Therefore, overcoming the competitive inhibition of myocardial cytochrome oxidase is desirable. This has been accomplished herein by increasing mitochondrial substrate concentration with an intravenous injection of exogenously reduced cytochrome c at 24 hours post CLP. Cytochrome c is reduced with excess ascorbate overnight at 4° C. The resultant concentration of reduced cytochrome c (ferrocytochrome c) is determined using the spectrophotometric absorbance at 550 nm.

Figure 4:
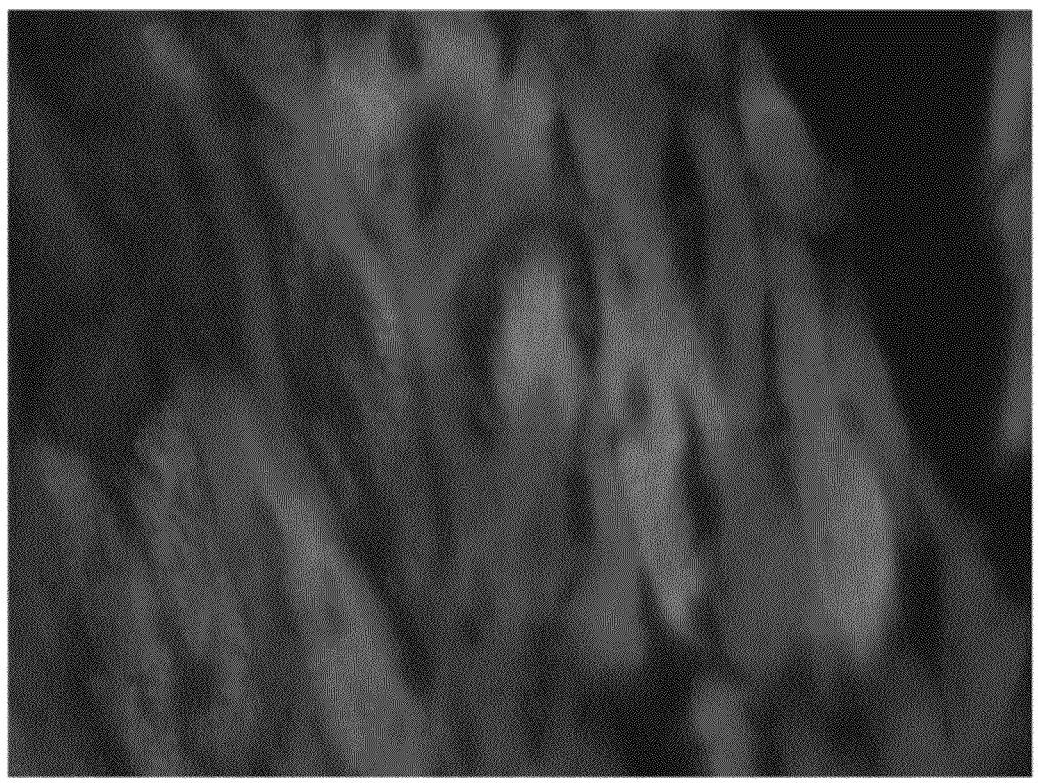
FIG. 4 is a micrograph of fluorescein-conjugated cytochrome c within mitochondria.

In order to determine if injected exogenous ferrocytochrome c gets into cardiomyocyte mitochondria, fluorescein was conjugated to cytochrome c. Fluorescein-conjugated cytochrome c (400 µg) was injected via tail vein into septic mouse at 24 hours post CLP. The animal was sacrificed 30 minutes after injection. The cardiac ventricles were harvested, fixed in 10% formalin at 4° C. overnight, paraffin embedded, and cut into 6 µm thick sections. The slices were then viewed using fluorescence microscopy. FIG. 4 demonstrates fluorescence in structures within the cardiomyocytes that resemble mitochondria (indicating fluorescein-conjugated cytochrome c within cardiomyocyte mitochondria).

Figure 5:
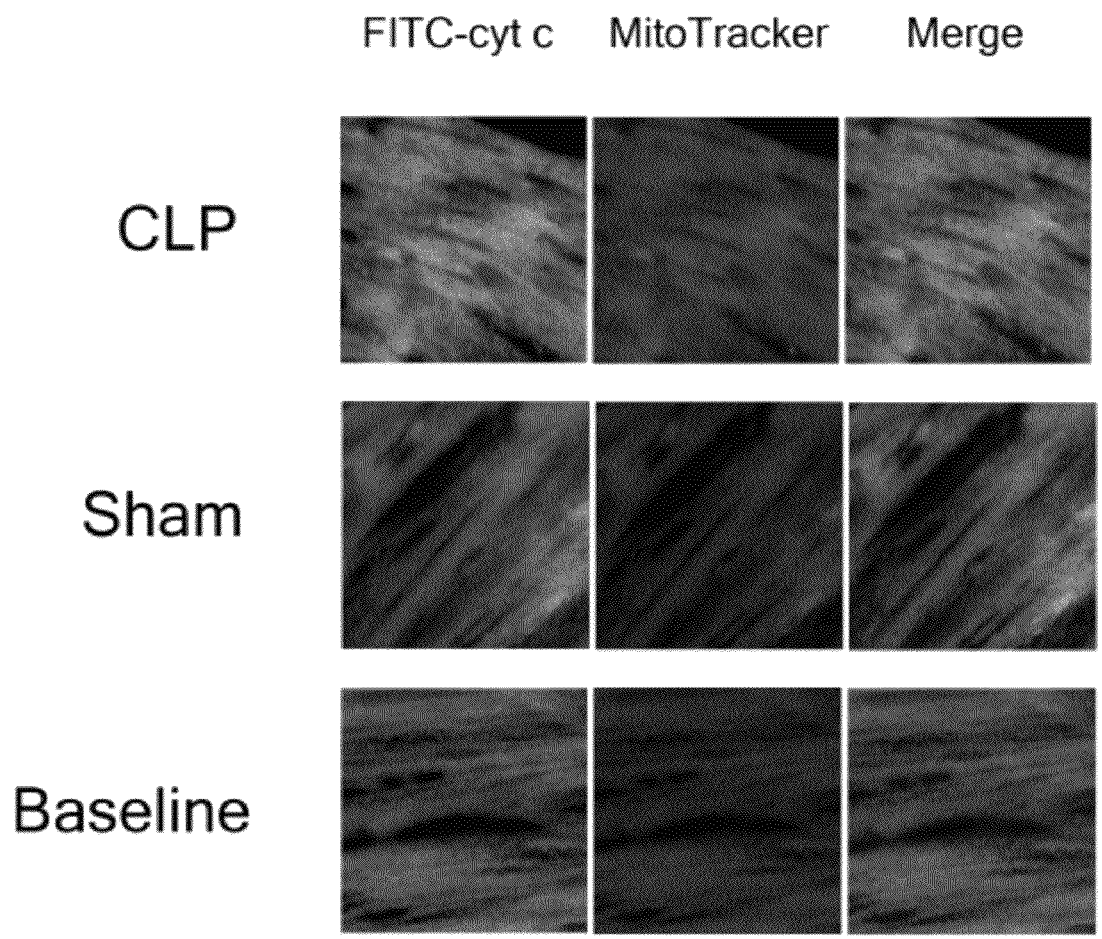
FIG. 5 is a fluorescent image of tissue co-injected with fluorescein-conjugated cytochrome c and Mitotracker Orange.

To confirm that cytochrome c does, in fact get into mitochondria, fluorescein-conjugated cytochrome c was co-injected with Mitotracker Orange (a probe that only fluoresces when oxidized by actively respiring mitochondria). Here, septic mice were injected at 24 hours post CLP, sham operated mice at 24 hours, and also a healthy non-operative control mouse was also assessed. Hearts were isolated 30 minutes after injection and paraffin embedded sections viewed with fluorescence microscopy. FIG. 5 demonstrates that fluorescein-conjugated cytochrome c co-localizes with Mitotracker Orange to cardiomyocyte mitochondria in all three groups.

Figure 6:
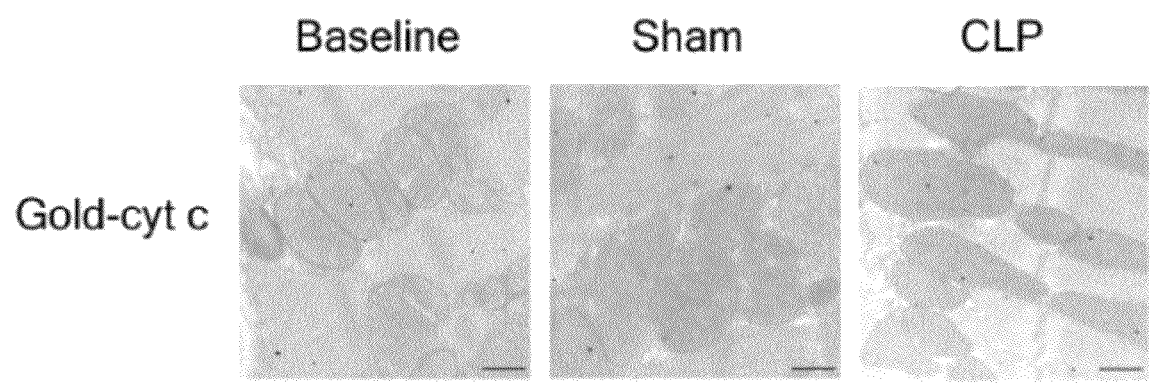
FIG. 6 is an image of cardiomyocytes depicting localization of gold-labeled cytochrome c within the mitochondria using electron microscopy (EM).

Mitochondrial localization was further confirmed with electron microscopy. 2 nm-colloid gold was conjugated to reduced cytochrome c and 800 µg injected into the tail vein of a septic mouse 24 hours following CLP. Cardiac ventricles were harvested 30 minutes after injection and the tissue was fixed overnight. Sections were prepared and enhanced with silver staining for 2 minutes. FIG. 6 demonstrates gold conjugated-cytochrome c within mitochondria of each mouse indicating that the injectate gets into cardiac mitochondria.

Figure 7:
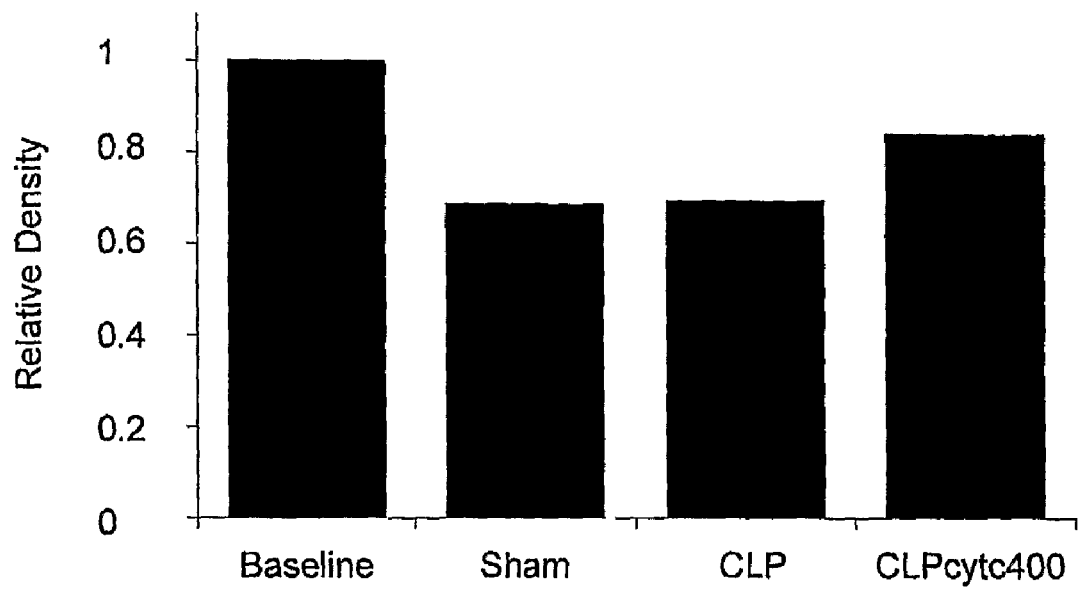
FIG. 7 provides a Western blot of cardiac mitochondrial cytochrome c levels following 400 µg (20 mg/kg) cytochrome c injection abd the relative densities graphically depicted.
Figure 7:
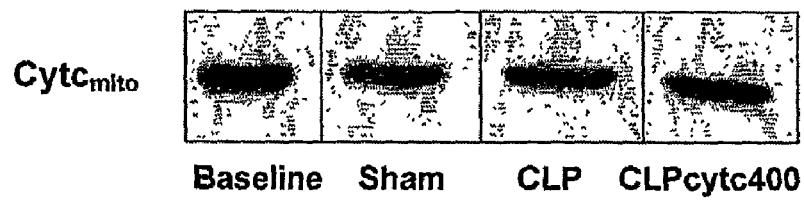

In order to quantify the mitochondrial levels of cytochrome c following injection, western blot analysis was performed on isolated ventricles 30 minutes following injection. Reduced cytochrome c (400 µg) was injected into the tail vein of a septic mouse at 24 hours post CLP and compared levels to a non-injected septic mouse and sham operated mouse at the same time point. Levels were also compared to a healthy baseline mouse (FIG. 7).

Figure 8:
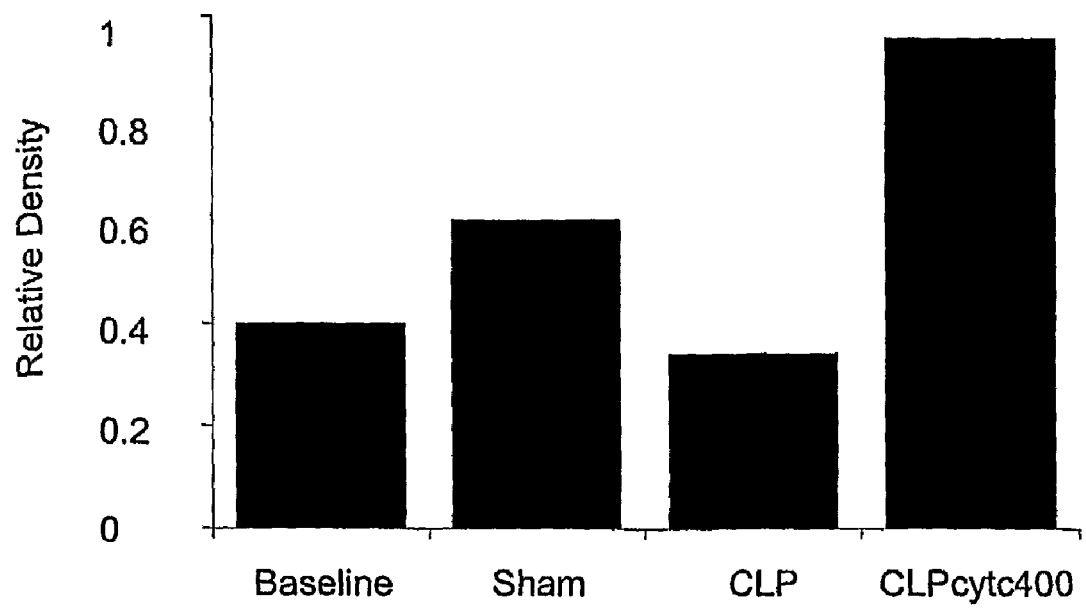
FIG. 8 provides a Western blot of mitochondrial cytochome c levels following 800 µg (40 mg/kg) cytochrome c injection and the relative densities graphically depicted.
Figure 8:
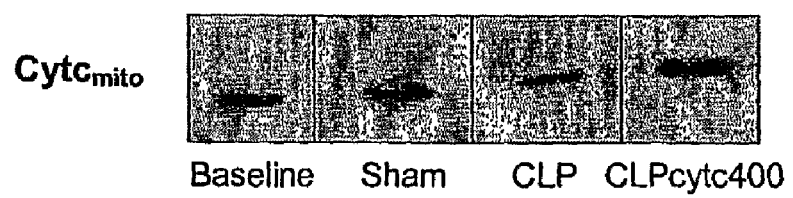

Although there was a slight increase in mitochondrial cytochrome c following a 400 µg injection compared to a non-injected septic mouse, levels still did not return to, or supercede baseline levels. Because the goal is to overcome competitive cytochrome oxidase inhibition, substrate levels (cytochrome c) should be greater than baseline. Therefore, the dose of exogenous cytochrome c was doubled to 800 µg. Again, a septic mouse was injected at 24 hours post CLP and western blot analysis was performed comparing the injected mouse to a non-injected septic control, sham operated control, and healthy, baseline non-operated control. The result was a >2-fold increase in mitochondrial cytochrome c levels compared to baseline and non-injected control (FIG. 8).

Figure 9:
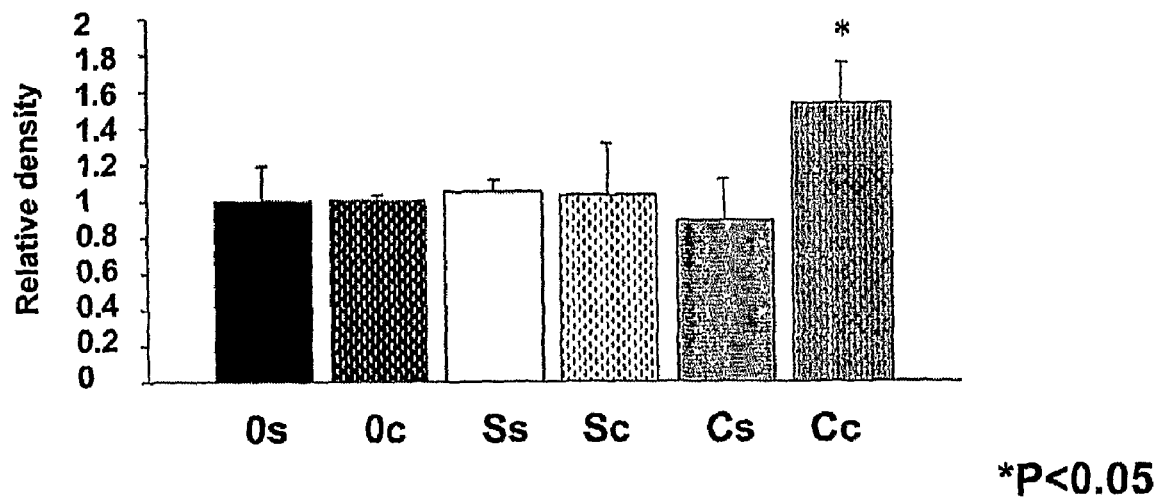
FIG. 9 provides a Western blot and graphical representation of mitochondrial cytochrom c levels following an 800 µg (40 mg/kg) injection.
Figure 9:
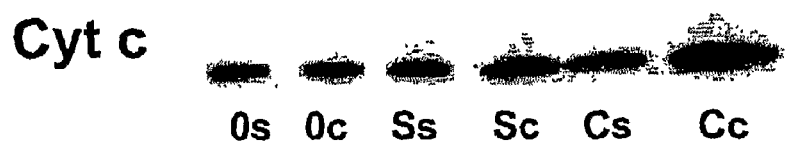

Having achieved significant levels of mitochondrial cytochrome c following injection, cardiac mitochondria was formally evaluated for cytochrome c levels using 6 cohorts of animals and 800 µg of injected exogenous cytochrome c. Septic mice injected with cytochrome c (Cc), septic mice sham injected with saline (Cs), sham operated mice injected with cytochrome c (Sc), sham operated mice sham injected with saline (Ss), healthy baseline non-operated mice injected with cytochrome c (0c), and healthy baseline non-operated mice sham injected with saline (0s) were evaluated. Septic and sham operated mice were injected at the 24 hour time point. All animal were sacrificed 30 minutes following injection. Cardiac ventricular mitochondria were isolated and western blots for cytochrome c were performed (N=5 per group). FIG. 9 demonstrates that mitochondrial levels of cytochrome c increased significantly in septic mice by 1.6 fold following an 800 µg injection of exogenous cytochrome c. Levels in healthy and sham mice did not change significantly.

Figure 10:
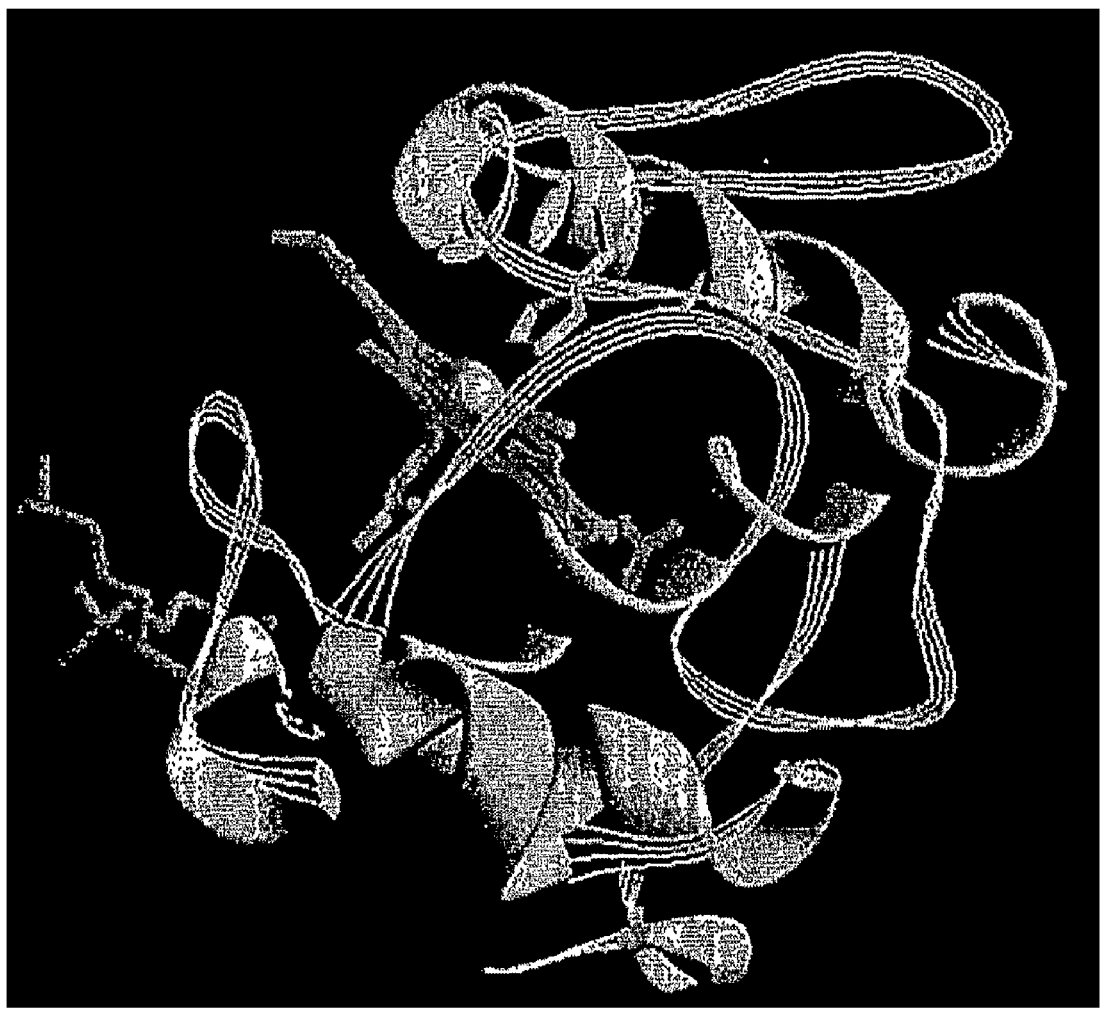
FIG. 10 is a drawing of the structure of cytochrome c. Heme c is covalently attached to the polypeptide.
Figure 11:
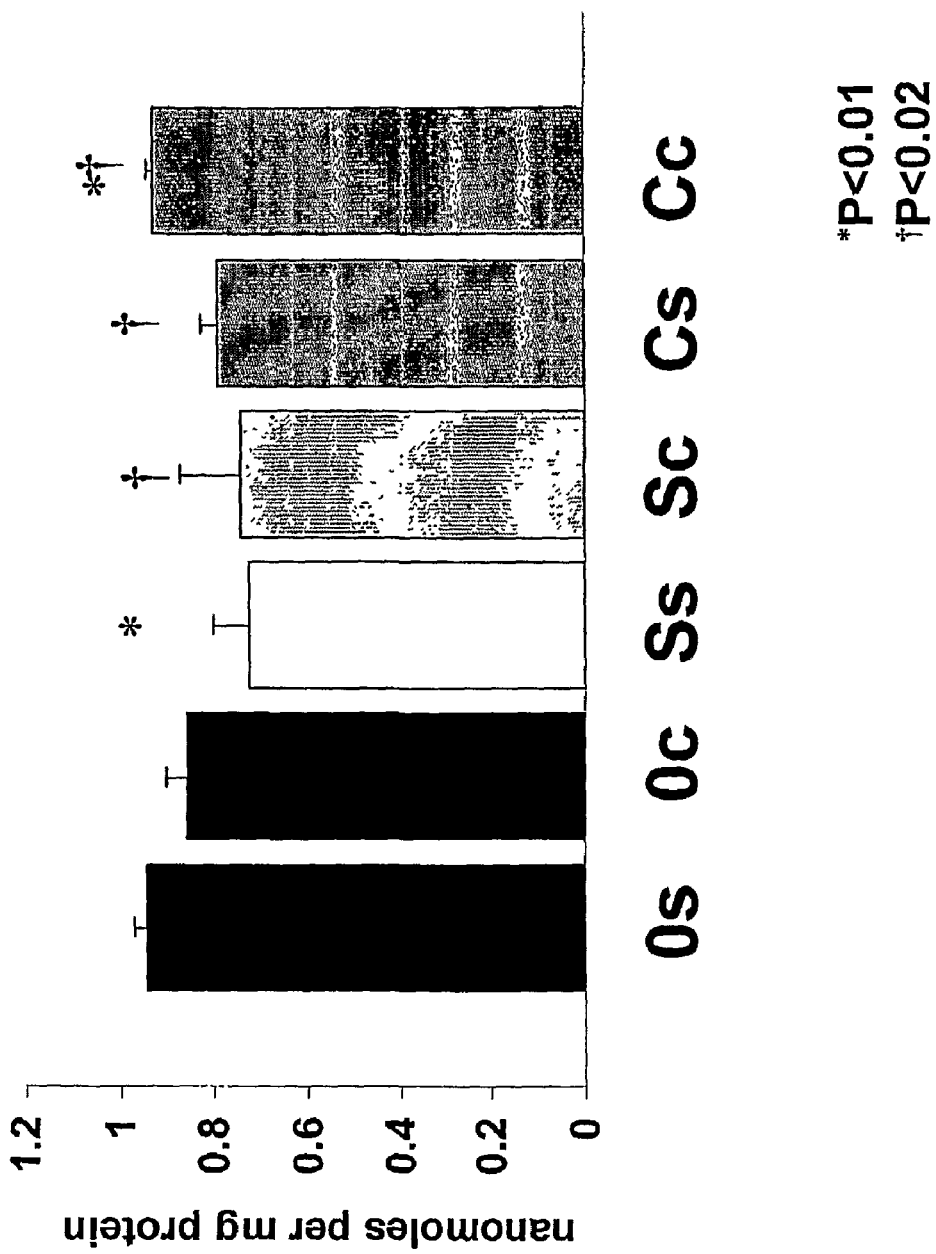
FIG. 11 is a graph depicting the heme c content in cardiomyocytes. Septic mice injected with cytochrome c (Cc), septic mice sham injected with saline (Cs), sham operated mice injected with cytochrome c (Sc), sham operated mice sham injected with saline (Ss), healthy baseline non-operated mice injected with cytochrome c (0c), and healthy baseline non-operated mice sham injected with saline (0s) were evaluated. N=5 per group. Values are means +/−SD.

Another way to quantify cytochrome c is to measure heme c, the prosthetic heme group covalently attached to the polypeptide (FIG. 10). To quantify cardiomyocyte heme c, mitochondria were isolated from cardiac ventricles and the difference in absorbance from 550 and 535 nm was determined using spectrophotometry. Heme c was quantified using the extinction coefficient of reduced cytochrome c. In the 6 cohorts of mice, the septic saline injected controls, and sham operated mice had relatively reduced amounts of cardiomyocyte heme c (FIG. 11). Injection of 800 µg cytochrome c in septic mice, however, restored heme c levels to baseline.

These data provide strong evidence that 800 µg of reduced cytochrome c injected into the tail vein of septic mice at 24 hours following CLP gets into cardiomyoctye mitochondria gaining access to cytochrome oxidase. Furthermore, the 800 µg dose repleats mitochondria with supranormal levels of cytochrome c. Since at 24 hours, myocardial cytochrome oxidase is competitively inhibited in sepsis, an increase in substrate availability should restore the enzyme's kinetic activity and increase oxygen consumption.

In order to evaluate this hypothesis, the 6 cohorts of mice previously examined (Septic mice injected with cytochrome c (Cc), septic mice sham injected with saline (Cs), sham operated mice injected with cytochrome c (Sc), sham operated mice sham injected with saline (Ss), healthy baseline non-operated mice injected with cytochrome c (0c), and healthy baseline non-operated mice sham injected with saline (0s)) were again studied. Mice were injected at the 24 hour time point and cardiac mitochondria were isolated 30 minutes after injection. Oxygen consumption was determined using 0.5 mg of fresh (less than 3 hours old) mitochondrial protein with a Clark-type electrode. Baseline cytochrome c-dependent respiration was determined in the presence of antimycin A (complex III inhibitor). Maximum respiration was then determined following addition of TMPD and ascorbate.

Figure 12:
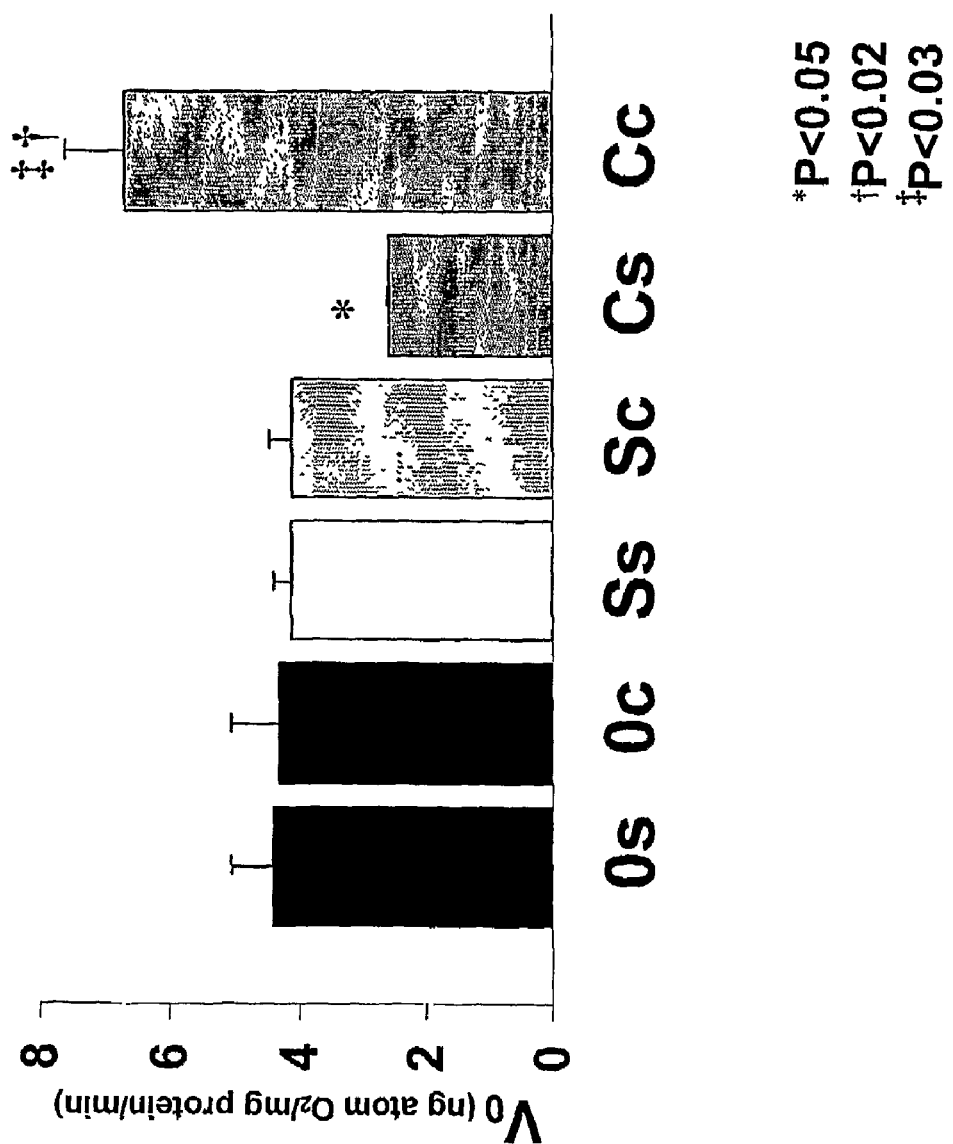
FIG. 12 is a graph depicting baseline cytochrome c-dependent oxygen consumption from the mice described in FIG. 11. N=5 per group. Values are means +/−SD.

Septic mice receiving a sham injection of saline had significantly diminished baseline cytochrome c-dependent oxygen consumption as expected (FIG. 12). Following injection with 800 µg of reduced cytochrome c, oxygen consumption significantly increased in cardiac mitochondria of septic mice. Baseline consumption was essentially unchanged from basal levels in sham operated mice and healthy mice injected with cytochrome c.

Figure 13:
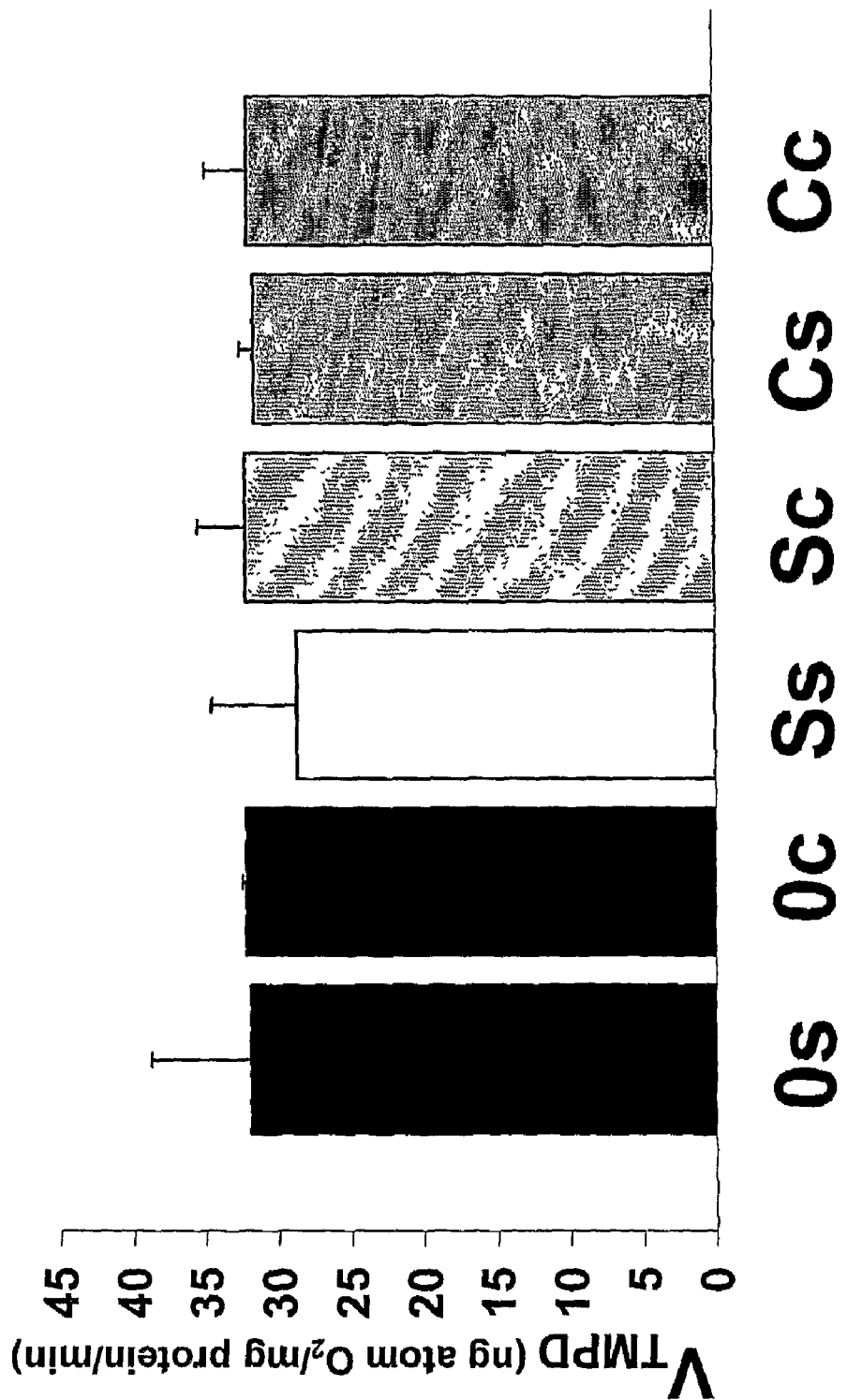
FIG. 13 is a graph depicting maximal cytochrome c-dependent oxygen consumption from the mice described in FIG. 11.

Maximal cytochrome c-dependent oxygen consumption was essentially at baseline in all groups (FIG. 13). This is consistent with the concept that myocardial cytochrome oxidase is competitively inhibited at the 24 hour time point and that maximally reduced cytochrome c (by the addition of TMPD and ascorbate) should allow the enzyme to achieve Vmax. Basal respiration is significantly decreased in septic mice and injection of cytochrome c during sepsis overcomes the inhibition and increases oxygen consumption in cardiac mitochondria dramatically.

Figure 14:
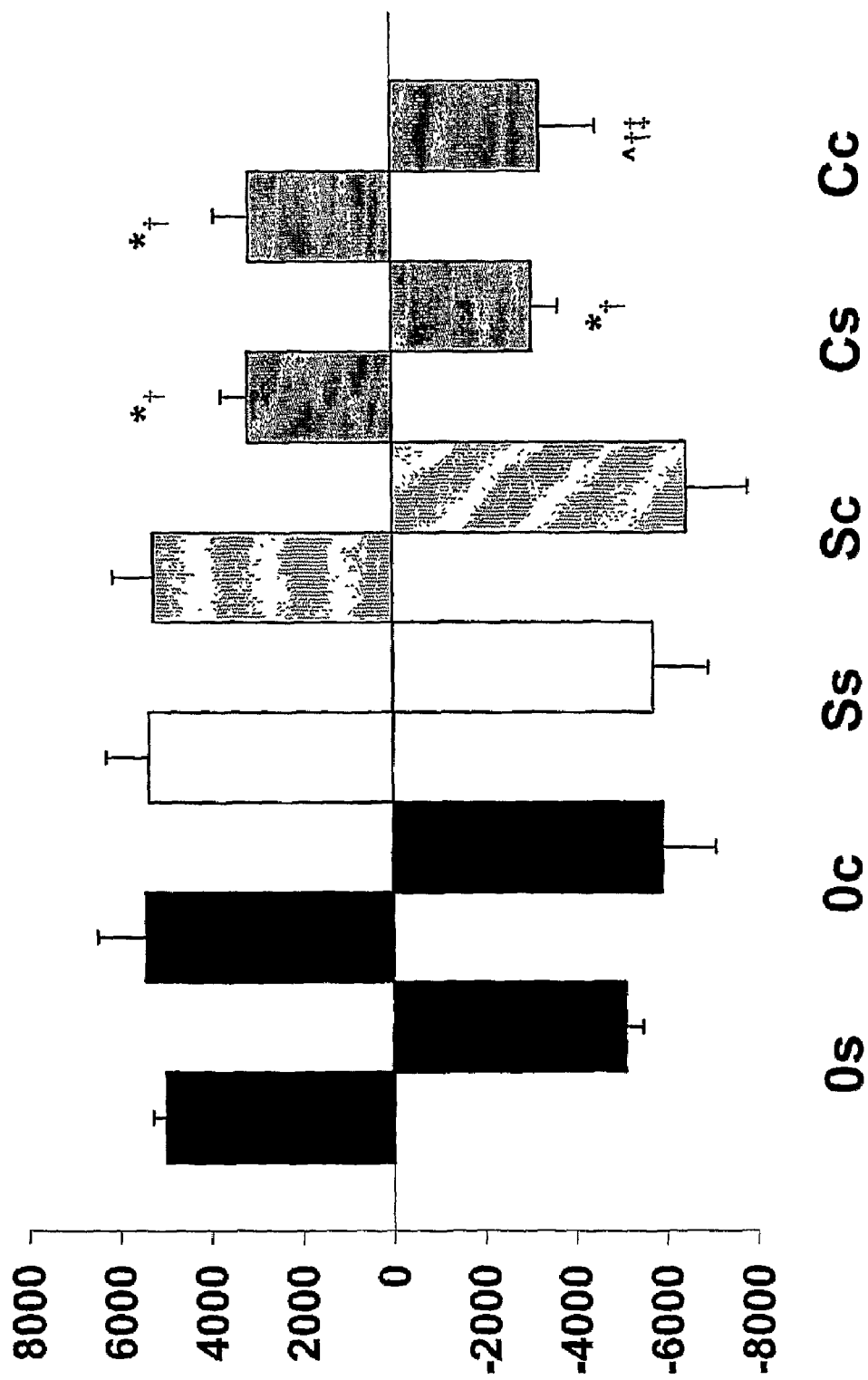
FIG. 14 is a graph depicting baseline $dP/dt_{max}$ and $dP/dt_{min}$ prior to injection. N=5 per group. Upgoing bars are $dP/dt_{max}$, downgoing bars are $dP/dt_{min}$. Values represent means +/−SD. Units are mmHg/sec. *$p<0.01$ vs. nonoperative controls (0s, 0c), †$p<0.05$ vs. sham controls (Ss, Sc), ‡$p<0.01$ vs. 0c, ^$p<0.05$ vs. 0s.
Figure 15:
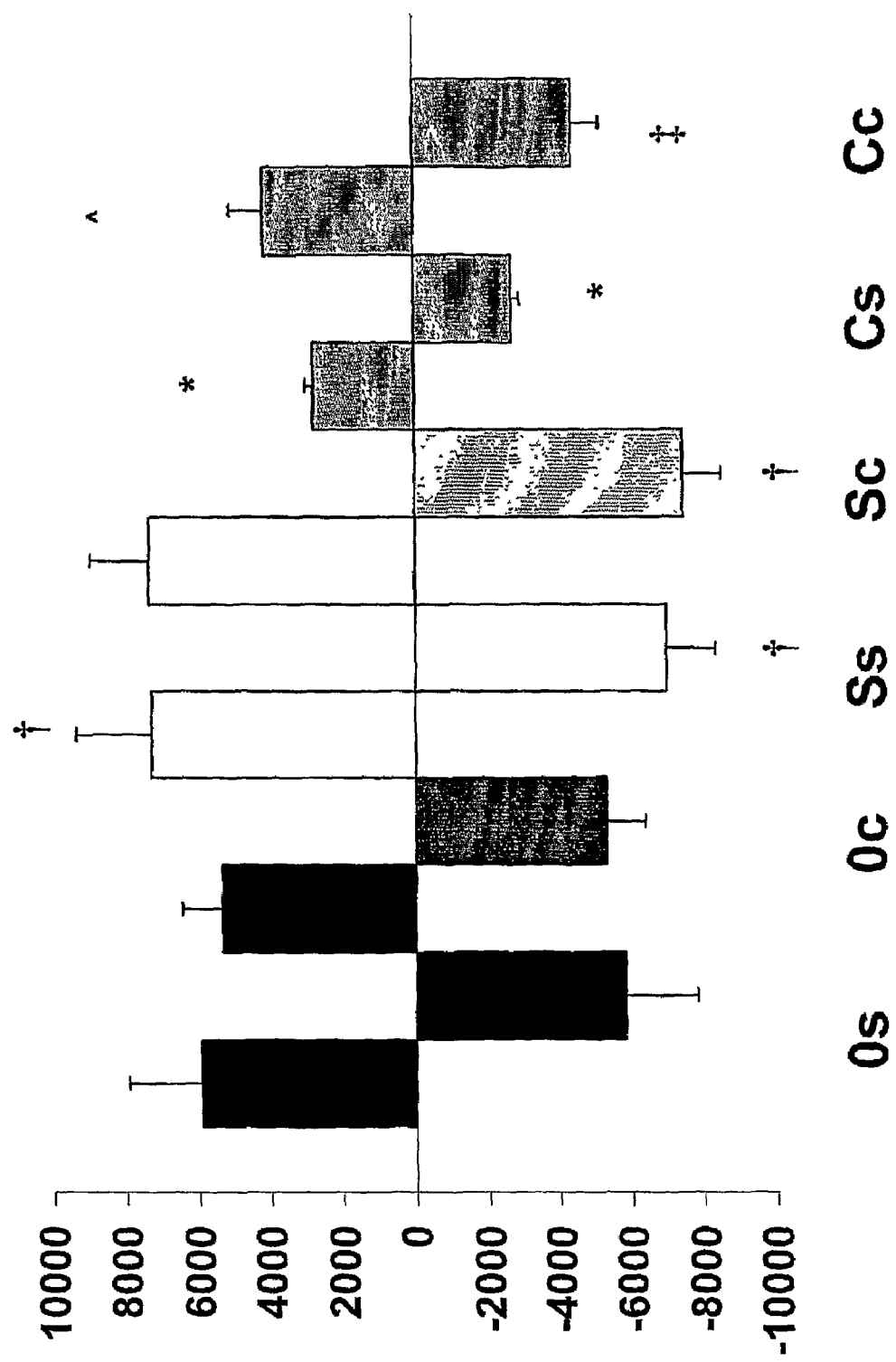
FIG. 15 is a graph depicting $dP/dt_{max}$ and $dP/dt_{min}$ post injection with cytochrome c (c) versus saline (s). N=5 per group. Values represent means +/−SD. Units are mmHg/sec. *$p<0.01$ vs. nonoperative controls (0s, 0c), †$p<0.05$ vs. CLP groups (Cs, Cc), ‡$p<0.01$ vs. Cs, ^$p<0.05$ vs. Cs.

In order for this increase in oxygen consumption to be physiologically significant, exogenous cytochrome c must have an effect on myocardial function. Therefore the left ventricular (LV) contraction and relaxation was measured using a 1.4 Fr. micromanometer catheter in vivo. After retrograde placement into the LV from the right carotid artery, pressure development was determined during isovolumic contraction ($dP/dt_{max}$) and relaxation ($dP/dt_{min}$), left ventricular systolic pressure (LVP), and the LV isovolumic relaxation constant (Tau). Heart rate (HR) and end-diastolic pressure (LVEDP) were measured at the steady state. The LV isovolumic relaxation constant (Tau) was calculated with use of the least-squares method for the LVP interval starting at $dP/dt_{min}$ based on the model of exponential decay with a zero asymptote. Following baseline measurement, each mouse randomly received 800 μg of exogenous cytochrome c (150 μL) or sham injection with equal volume of saline via tail vein. Hemodynamic parameters were again recorded thirty minutes following injection. Table 1 demonstrates that there was no statistical difference in baseline HR, LVEDP, and tau between all groups. In both CLP groups, baseline LVP was significantly decreased compared to baseline and sham mice (Table 1). FIG. 14 shows no difference in baseline $dP/dt_{max}$ and $dP/dt_{min}$ between sham and healthy nonoperative controls. As expected, baseline $dP/dt_{max}$ and $dP/dt_{min}$ were significantly decreased in CLP mice (FIG. 14). However, there was no difference in baseline $dP/dt_{max}$ and $dP/dt_{min}$ between CLP groups (FIG. 14). Following injection with exogenous cytochrome c in CLP mice, LVP, $dP/dt_{max}$ and $dP/dt_{min}$ significantly increased compared to saline injection (Table 1, FIG. 15). These increases approached baseline values of healthy nonoperative and sham controls and represented >45% improvement in $dP/dt_{max}$ and $dP/dt_{min}$. Furthermore, this improvement in ventricular contractility and relaxation occurred without significant impact on HR, LVEDP, and tau (Table 1). There was no appreciable change in HR, LVEDP, LVP, tau, $dP/dt_{max}$, or $dP/dt_{min}$ in CLP mice that received saline injection (Table 1, FIG. 15). In addition, there was no significant effect of either saline or cytochrome c on any of the parameters in healthy non-operative controls (baseline, Table 1, FIG. 15). Sham animals, however, had an increase in both $dP/dt_{max}$ and $dP/dt_{min}$ that was equivalent following saline or cytochrome c injection (FIG. 15). Since sham operation represents a mild inflammatory response, this effect most likely represents the result of volume infusion, as there was no difference based on type of injectate. Of note, tau did increase slightly following cytochrome c injection in sham mice as compared to saline injection (Table 1). Taken together, these data indicate that exogenous cytochrome c dramatically improves ventricular contractility and relaxation in septic mice.

TABLE 1

Hemodynamic Parameters Following Cytochrome C (cyt c) Injection Versus Equal Volume of Saline

| | | HR (bpm) | LVP (mmHg) | LVEDP (mmHg) | Tau (ms) |
|---|---|---|---|---|---|
| Base-line | Pre saline | 387 +/− 29 | 91 +/− 19 | 5 +/− 2 | 7.7 +/− 2.6 |
| | Post saline | 404 +/− 19 | 99 +/− 22 | 5 +/− 1 | 9.0 +/− 1.4 |
| Base-line | pre cyt c | 433 +/− 44 | 91 +/− 12 | 5 +/− 3 | 8.2 +/− 2.7 |
| | Post cyt c | 437 +/− 91 | 91 +/− 17 | 4 +/− 2 | 7.4 +/− 2.7 |
| Sham | Pre saline | 384 +/− 24 | 89 +/− 8 | 5 +/− 0 | 8.3 +/− 0.6 |
| | Post saline | 425 +/− 76 | 99 +/− 13 | 9 +/− 6 | 7.6 +/− 3.3 |
| Sham | pre cyt c | 437 +/− 62 | 90 +/− 10 | 6 +/− 2 | 8.9 +/− 0.2 |
| | Post cyt c | 436 +/− 45 | 107 +/− 9 | 8 +/− 3 | 11.5 +/− 1.3^ |
| CLP | pre saline | 472 +/− 18 | 64 +/− 7* | 6 +/− 3 | 8.4 +/− 3.3 |
| | post saline | 446 +/− 12 | 61 +/− 6* | 7 +/− 3 | 10.0 +/− 1.0 |
| CLP | pre cyt c | 420 +/− 51 | 67 +/− 9* | 6 +/− 2 | 8.3 +/− 2.9 |
| | post cyt c | 428 +/− 58 | 75 +/− 8†‡ | 8 +/− 2 | 8.7 +/− 3.0 |

Baseline represents nonoperative controls, sham is sham operated mice, CLP is septic mice.
Baseline measurements were taken at steady state prior to injection (pre) and after injection (post).
Heart rate (HR), left ventricle pressure (LVP), left ventricle end diastolic pressure (LVEDP), and tau were measured.
Values are means +/− st dev.
*$p < .05$ vs. baseline and sham,
†$p < .05$ vs. sham post cyt c,
‡$p < .05$ vs. CLP post saline,
^$p < .05$ vs. sham pre cytc.

This improvement in cardiac function is only significant if it has an impact on mortality. Thus, we evaluated the effect of exogenous cytochrome c on survival following CLP. Survival following double puncture CLP is 50% at 24 hours, 25% at 48 hours, 10% at 72 hours and almost 0% by 96 hours. Following cytochrome c injection (800 μg) at 24 hours, 82% of mice survived to 48 hours, 66% survived to 72 hours, and 50% survived to the 96 hour time point (N=20). Thus, exogenous cytochrome c improved survival dramatically. Importantly, cytochrome c had no effect on mortality of healthy non-operative and sham operated controls (0% mortality, N=20 per group).

In summary, the data demonstrate that injected exogenous cytochrome c gain access to the cardiac mitochondria of septic animals, increases oxygen consumption, thereby dramatically improving myocardial function and enhancing survival.

EXAMPLE II

The response of myocardium to ischemia is strikingly similar to sepsis-associated myocardial depression. Hypoperfused myocardium, like septic myocardium, is dysfunctional yet viable, with preserved cellular ATP. During ischemia and hypoxia, reversibly hypocontractile cardiomyocytes maintain viability by down-regulating oxygen consumption, energy requirements, and ATP demand. This adaptive response is known as myocardial hibernation. Although well described in the setting of ischemia and hypoxia, myocardial hibernation has not been evaluated in other disease processes. Recent postmortem examination of septic patients revealed histologic absence of injury and little cell death despite profound organ dysfunction. Thus it is possible that sepsis-associated organ dysfunction may reflect underlying cellular hibernation where cells maintain viability by reducing oxygen consumption and energy requirements. A key difference between sepsis-associated myocardial depression and ischemic myocardium is impaired oxygen utilization, not oxygen supply. Decreased oxygen delivery is known to lead to hibernation. A potential cellular sensor for decreased oxygen tension is cytochrome oxidase, the terminal oxidase of the electron transport chain. Following the addition of azide, a specific irreversible inhibitor of cytochrome oxidase, normoxic cardiomyocytes become reversibly hypocontractile, mimicking the hibernation response to hypoxia. It has been previously reported that irreversible myocardial cytochrome oxidase inhibition occurs in a murine model of sepsis. Although the causes of noncompetitive inhibition during sepsis remain unknown, this may represent a mechanism underlying cytopathic hypoxia. It is highly plausible that irreversible cytochrome oxidase inhibition during sepsis, like azide-induced inhibition during normoxia, leads to myocardial hibernation. During ischemia, hibernating cardiomyocytes undergo characteristic cellular and metabolic alterations. To maintain viability, these cells rely on anaerobic glycolysis for ATP production and switch their primary substrate utilization from fatty acids to glucose. The myocardial specific glucose transporters, GLUT1 and GLUT4, facilitate increased myocardial glucose uptake. During ischemia and hypoxia, the more abundant transporter, GLUT4, translocates from intracellular vesicles to the plasma membrane and is up-regulated. In addition, hibernating myocardium demonstrates increased glycogen deposition in the perinuclear region and between myofibrils. Here the septic heart was evaluated for evidence of myocardial hibernation in mice subjected to cecal ligation and double puncture (2CLP), a well-validated, reproducible animal model of sepsis. Importantly, three novel, clinically relevant, noninvasive techniques were employed to assess for hibernation: magnetic resonance imaging (MRI), positron emission tomography (PET), and single photon emission computed tomography (SPECT). Because hibernating myocardium is, by definition, hypocontractile, MRI assessment of cardiac function was first used to determine whether 2CLP induces ventricular dysfunction. Septic myocardium was then evaluated for the characteristic cellular alterations seen during hibernation. Three specific questions were addressed: first, whether sepsis increases myocardial glucose uptake as determined with PET scanning; second, whether 2CLP increases steady state levels of ventricular GLUT1 and GLUT4; and third, whether sepsis leads to increased myocardial glycogen deposition. Because hyperglycemia can increase myocardial glucose uptake in normoxic cardiomyocytes, blood glucose levels were assessed in septic mice. In addition, although hypoxia and ischemia are defined by a defect in oxygen delivery, cytopathic hypoxia occurs in the setting of preserved oxygen tension and organ perfusion. Thus, it determined whether arterial oxygen tension and myocardial perfusion were maintained following 2CLP.

Material and Methods

Induction of Sepsis:

Sepsis was induced using the methods described in Example 1. At least three animals per group were studied. All studies were performed at 48 hrs post procedure. This time point was chosen based on the onset of myocardial cytochrome oxidase irreversible inhibition when mortality rate is 75%. All animals were killed with 50 mg/kg intraperitoneal pentobarbital.

Electrocardiogram-Gated MRI:

Under isoflurane general anesthesia (up to 1.5%), platinum subdermal needle electrodes were inserted in the right forelimb and left hindlimb and a thermistor temperature probe was placed rectally to monitor electrocardiogram and temperature, respectively. During preparation, mice were warmed by a circulating water blanket to maintain 37° C. body temperature. MRI images were acquired as previously described in Zhou et al. (Magn Reson Med 2003; 49:760-764). All images were generated on 4.7-T horizontal bore INOVA spectrometer (Varian, Palo Alto, Calif.) equipped with 12-cm gradients having a maximum strength of 25 gauss/cm and a rise time to full amplitude of 200 μsecs. Either a single-turn elliptical surface coil (2.5×3.5 cm) or a linearly polarized birdcage coil (3.2×5.0 cm) was used for transmission and reception. Both coils were designed and constructed at the University of Pennsylvania. A series of gradient echo scout images were generated to determine the long axis of the heart. Short-axis images were then planned from the long-axis scouts. Electrocardiogram-gated images were acquired. Single slice sequences were repeated multiple times with the slice position shifted by one slice thickness, permitting acquisition of contiguous slices. Seven to nine slices were needed to span the entire left ventricle (LV). The global cardiac output was determined using the Image Browser (Varian, Palo Alto, Calif.) program. The borders of the LV endocardium were manually traced on the end-diastolic and end systolic images of each slice, and their areas were tabulated. LV cavity volumes at end diastole and end-systole were estimated by summing the differences within endocardial areas from the base to the apex and then multiplying by the slice thickness. The difference between end-diastolic volume and end systolic volume defined the stroke volume. Cardiac output (mL/min) was determined by multiplying stroke volume by the average heart rate. Five septic, five nonoperated, and three sham-operated mice were studied.

PET Scanning Using 18-Fluorodeoxyglucose (FDG):

Under isoflurane general anesthesia (up to 1.5%), glucose utilization images were obtained 60 mins following 18-FDG (100-200 μCi) tail vein injection. Each animal was scanned for 15 minutes. Mouse PET imaging was performed on a high-resolution dedicated small animal PET scanner, based on the Philips Mosaic system (Philips Medical Systems, Cleveland, Ohio). The animal scanner used a discrete 2×2×10 mm$^3$ L-YSO Anger-logic detector; had a diameter of 21 cm, transverse field of view of 12.8 cm, and axial length of 12.8 cm; and operated exclusively in three-dimensional volume imaging mode. Spatial resolution was 2 mm in the central region of the field of view, and system sensitivity was 5.45 cps/kBq. Images were reconstructed using the row action maximum likelihood algorithm. Transverse thoracic images were used for quantitation. At least three transverse slices were evaluated. Circular regions of interest were drawn around the heart and neighboring lung (background). Densities were quantified and corrected for background scatter. Three mice per group were compared.

Blood Glucose and $PaO_2$ Measurement:

Following intraperitoneal pentobarbital (50 mg/kg), during spontaneous ventilation in room air, and before apnea, the midline abdominal incision was opened and 0.2 mL of blood was sampled from the descending aorta. Glucose was measured using a glucometer (SureStepFlexx Professional Blood Glucose Monitoring System, LifeScan, Milpitas, Calif.). $Pao_2$ was measured using a blood-gas analyzer (I-STAT Portable Clinical Analyzer, G3+ cartridge, I-STAT Corporation, East Windsor, N.J.). Three mice per group were evaluated.

GLUT4 and GLUT1 Protein Immunoblotting:

Immunoblots were performed as previously described. Following euthanasia with intraperitoneal pentobarbital (50 mg/kg), the heart was excised and cardiac ventricles were perfused with saline and immediately placed in iced phosphate buffered saline. Ventricles were homogenized in H medium (70 mM sucrose, 220 mM mannitol, 2.5 mM 4-[2-hydroxyethyl]-1-piperazineethanesulfonic acid, pH 7.4, and 2 mM EDTA). Cytosol was isolated by differential centrifugation, and cytosolic protein concentration was determined. Then 10-μg samples of cytosolic protein were subjected to sodium dodecyl sulfate-acrylamide gel electrophoresis and immunoblotting. Blots were labeled with a primary polyclonal antibody to mouse GLUT4 and GLUT1 (Santa Cruz Biotechnology, Santa Cruz, Calif.) and secondarily exposed to rabbit antimouse immunoglobulin G (Santa Cruz Biotechnology). The signal was detected with enhanced chemiluminescence (Amersham Pharmacia Biotech, Piscataway, N.J.), and densities were measured using scanning densitometry. Three animals per group were studied.

Myocardial Glycogen Content:

Following euthanasia with intraperitoneal pentobarbital (50 mg/kg), the heart was excised and cardiac ventricles were immediately placed in iced 10% formalin. Hearts were fixed in 10% formalin at 4° C. overnight, paraffin embedded, and cut into 6-µm thick sections. Sections were slide mounted and stained with hematoxylin and eosin and periodic acid-Schiff. Ten high-power fields were selected at random from each representative section (Nikon E600 Eclipse microscope with a CoolSnap CF high-resolution CCD camera, Roper Scientific, Tucson, Ariz.). Images were acquired using IPLap image acquisition/analysis software (Scanalytics, Fairfax, Va.).

SPECT Imaging With (99m)Tc Sestamibi:

Under general anesthesia with isoflurane (up to 1.5%), myocardial perfusion images were obtained 60 mins after (99m)Tc sestamibi (1 mCi) tail vein injection, and each animal was scanned for 1 hr. Cardiac SPECT imaging was performed on a Prism 3000XP triple-headed gamma camera (Philips Medical Systems, Cleveland, Ohio), equipped with custom-made tungsten knife edge pinhole collimators (Nuclear Fields, Des Plaines, Ill.) (21-24). The focal length of the collimators was 24 cm, with a radius of rotation of 3 cm and a pinhole diameter of 2 mm, giving a spatial resolution of 2.5 mm. The acquisition parameters included a continuous mode with 120 projection angles over a 360° arc to obtain data in a 128×128 matrix with a pixel size and slice thickness of 3.56 mm. The images were then reconstructed using ten iterations of a simultaneous algebraic reconstruction technique. Correction for center of rotation error was performed by scanning a thin line source and iteratively adjusting the center-of-rotation offsets until the reconstructed image was a point, rather than an annulus. Images consisted of a matrix of 128×128×128 with an isotropic voxel size of 0.45 mm. Attenuation and scatter correction were not performed on the SPECT data. The SPECT images of the mouse were reoriented to give long- and short-axis slices through the heart. Annular regions of interest were placed over at least five short-axis slices of the myocardium, avoiding the region of the heart closest to the liver. Irregular regions were drawn over the lung, covering at least four slices. The ratio of heart uptake to that in the lungs was used as a semiquantitative index of myocardial perfusion. Three mice per group were evaluated.

Data Analysis:

All data are presented as mean±SD. Statistical significance was determined using Student's t-test. Significance was set at $p<0.05$.

Results

Cardiac Function:

Septic mice demonstrated cardiac dysfunction compared with nonoperative (baseline) and sham-operated controls. Cardiac output decreased 33% following 2CLP compared with baseline and 23% compared with sham-operated mice ($p<0.005$ and $p<0.02$, respectively; Table 2). Depressed cardiac output following 2CLP was due to significantly diminished left ventricular stroke volume ($p<0.05$ vs. baseline; Table 2). Although there was a trend toward a slower heart rate in septic mice, there was no significant difference between groups (Table 2).

TABLE 2

| Cardiac Performance | | | |
|---|---|---|---|
| Variable | Baseline | Sham | 2CLP |
| CO, mL/min | 15 ± 2 | 13 ± 1 | 10 ± 1[a,b] |
| SV, µL | 31 ± 6 | 26 ± 2 | 23 ± 4[c] |
| HR, min$^{-1}$ | 460 ± 50 | 490 ± 47 | 400 ± 82 |

2CLP, double cecal ligation and puncture;
CO, cardiac output;
SV, stroke volume;
HR, heart rate.
[a] $p < .02$ vs. sham;
[b] $p < .005$ vs. baseline;
[c] $p < .05$ vs. baseline. Ventricular function of nonoperative controls (baseline n = 5), sham-operated subjects (sham n = 3), and septic mice (2CLP, n = 5) determined in vivo with electrocardiogram-gated magnetic resonance imaging.
Values are means ± SD.

Myocardial Glucose Uptake:

Sepsis increased myocardial 18-FDG density more than 1.5-fold compared with baseline and sham operation ($p<0.001$; FIG. 16, A and B). There was no difference in 18-FDG density between sham-operated mice and baseline (FIG. 16, A and B). As reported previously, 2CLP significantly decreased serum glucose levels relative to both baseline and sham operation (62.5±3.5 vs. 191.5±3.5 [$p<0.005$] and 212.5±30.4 mg/dL [$p<0.02$], respectively) (Deutschman C S et al., Circ Shock 1993; 40:295-302 and Deutshman C S et al., Am j Physiol 1995; 269:R584-R591). Thus, the sepsis-associated increase in myocardial glucose uptake did not reflect systemic hyperglycemia.

Myocardial GLUT1 and GLUT4:

Steady-state levels of GLUT4 increased 1.6-fold following 2CLP vs. baseline and 1.3 fold compared with sham operation ($p<0.02$; FIG. 16, C and D). GLUT4 levels following sham operation were not significantly different from baseline. Levels of GLUT1, the less abundant transporter, decreased following 2CLP and were relatively increased following sham operation (FIG. 16, C and D).

Figure 16A:
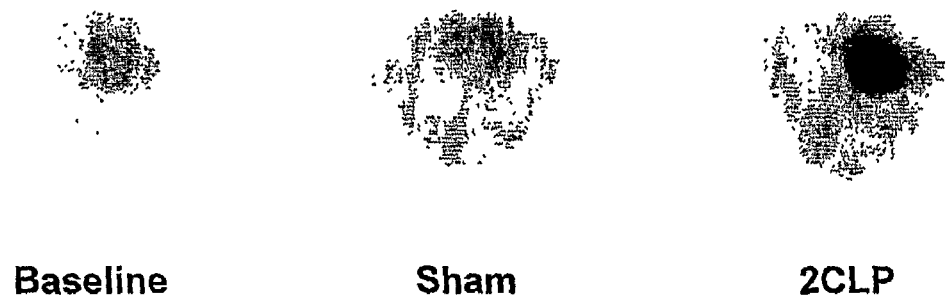
FIGS. 16A-E pertain to cellular and metabolic alterations observed in the septic heart.
Figure 16B:
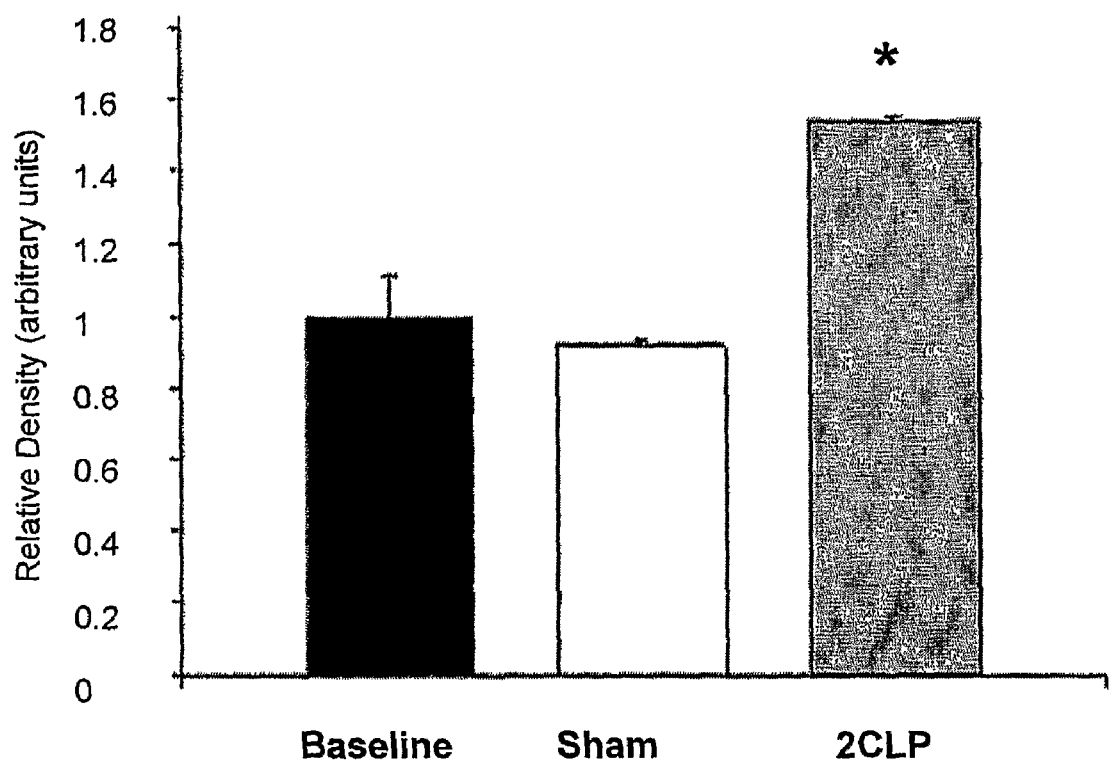
Figure 16C:
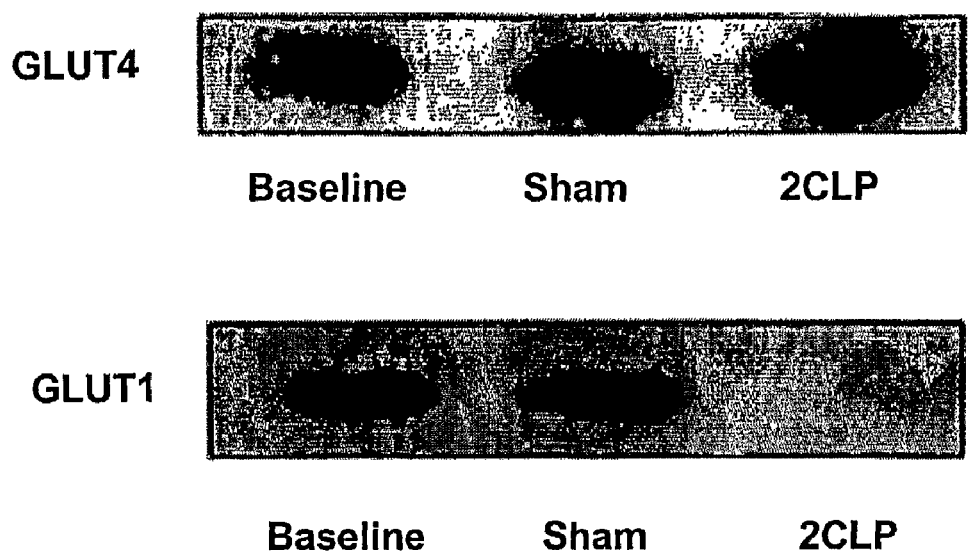
Figure 16D:
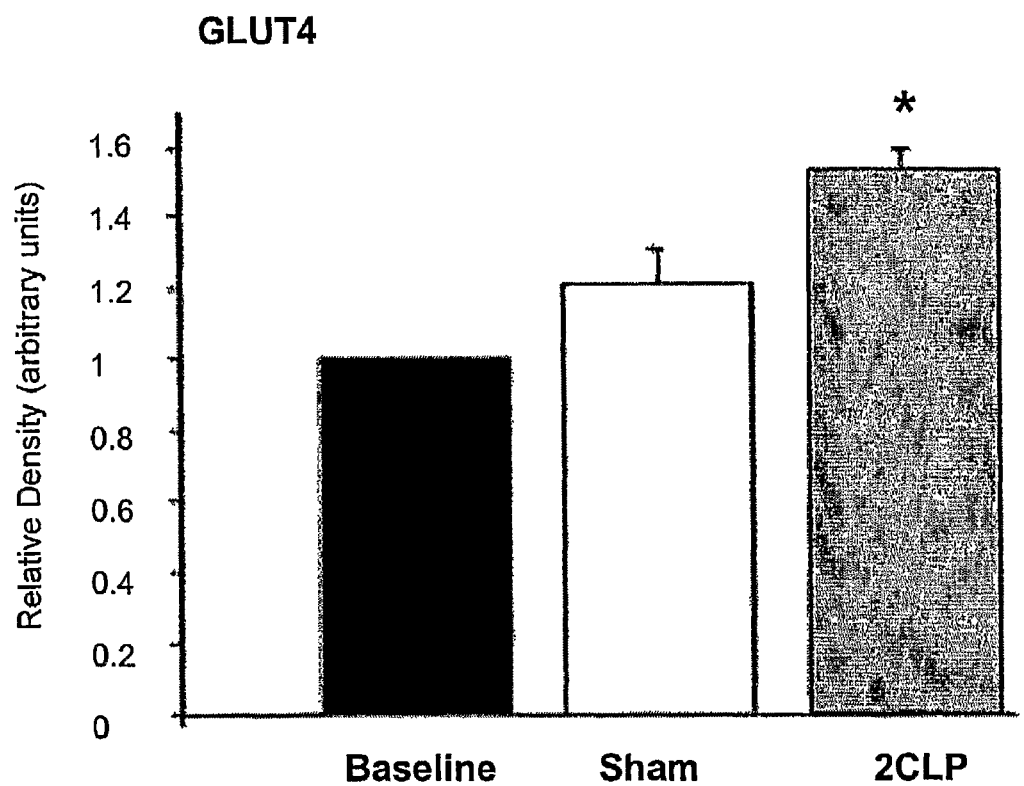
Figure 16D:
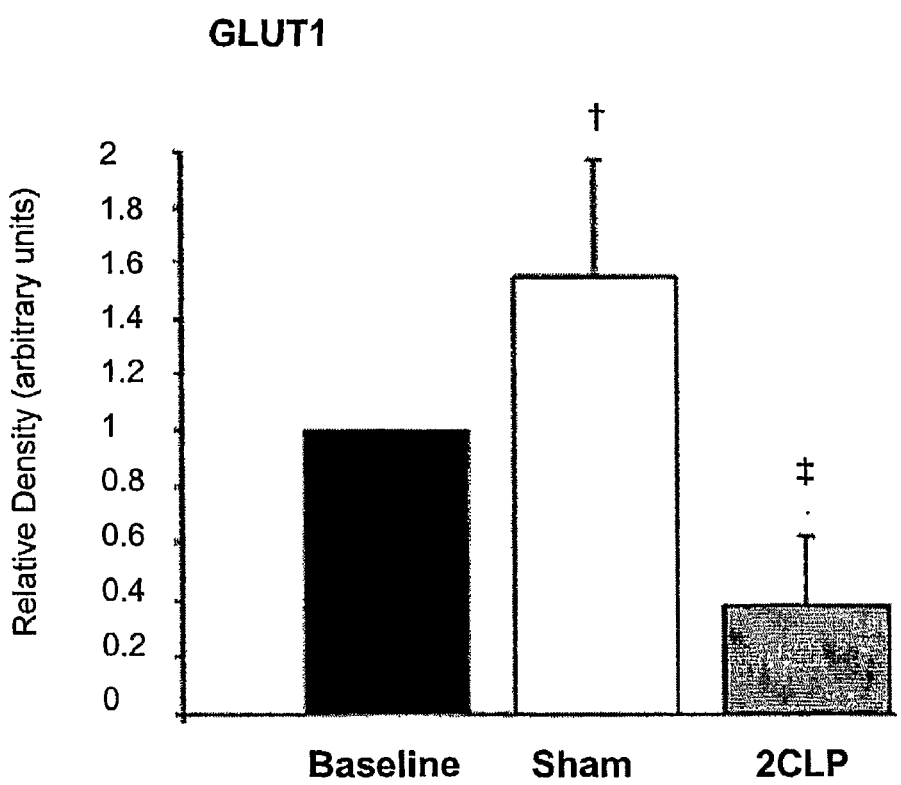
Figure 16E:
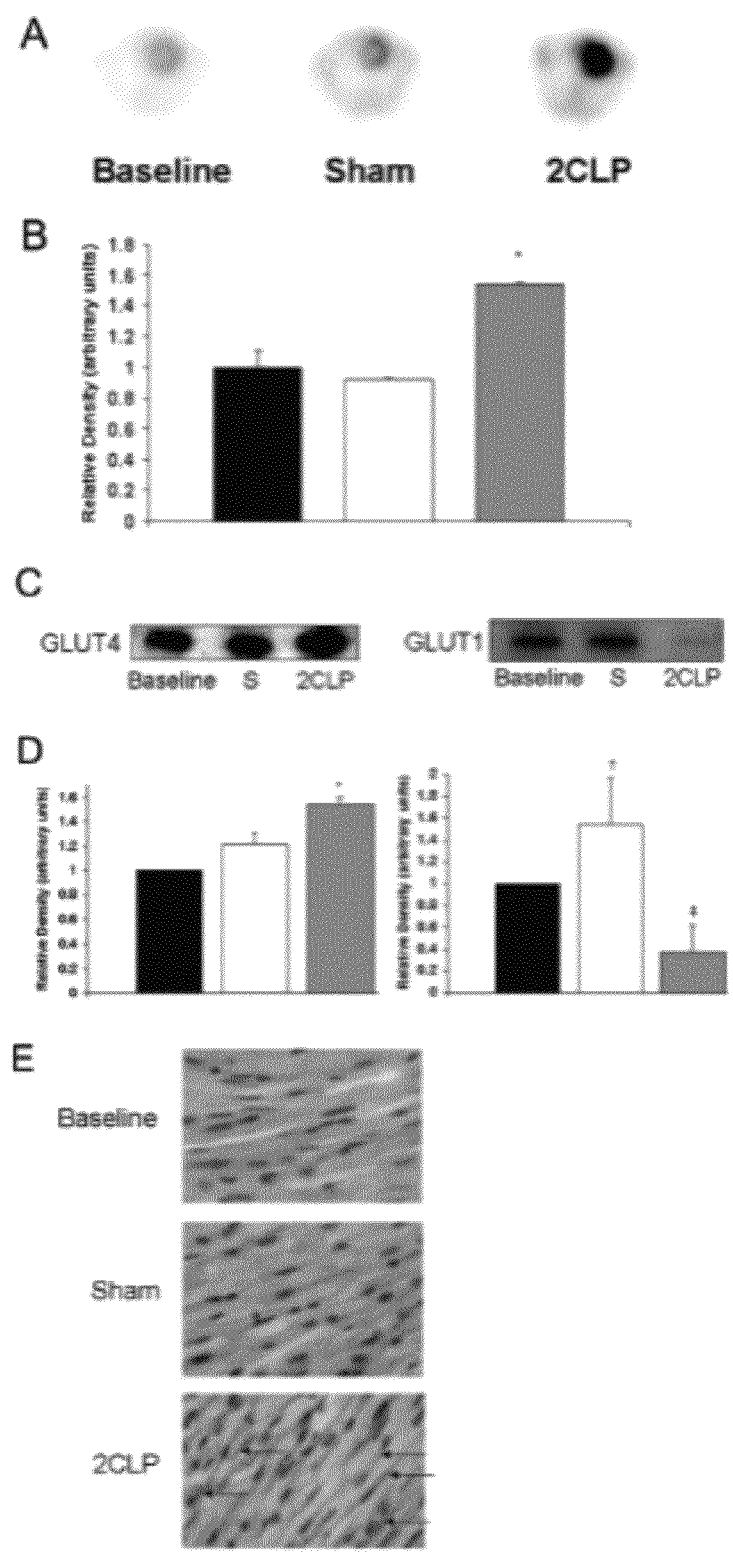
Figure 17A:
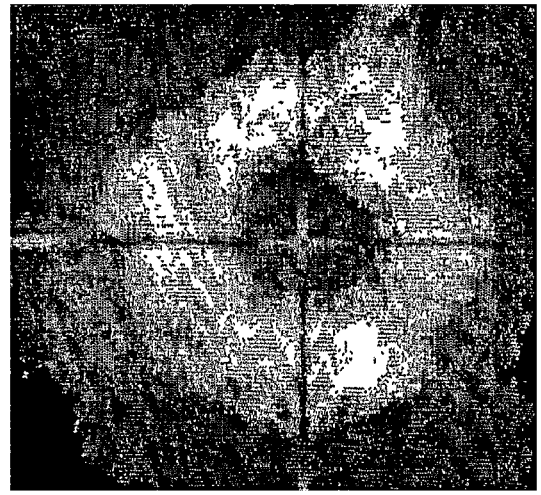
FIGS. 17A-B relate to in vivo myocardial perfusion.
Figure 17A:
Figure 17A:
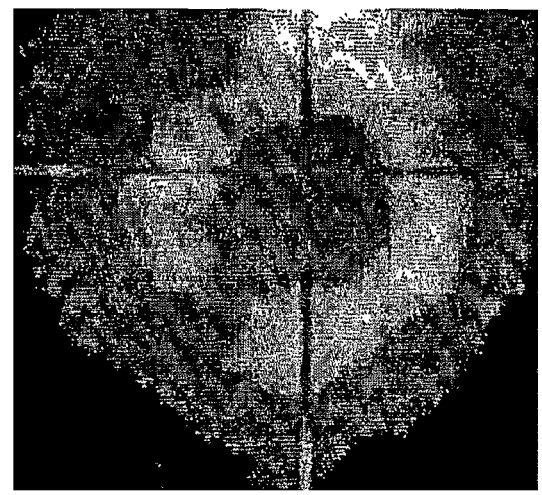
Figure 17B:
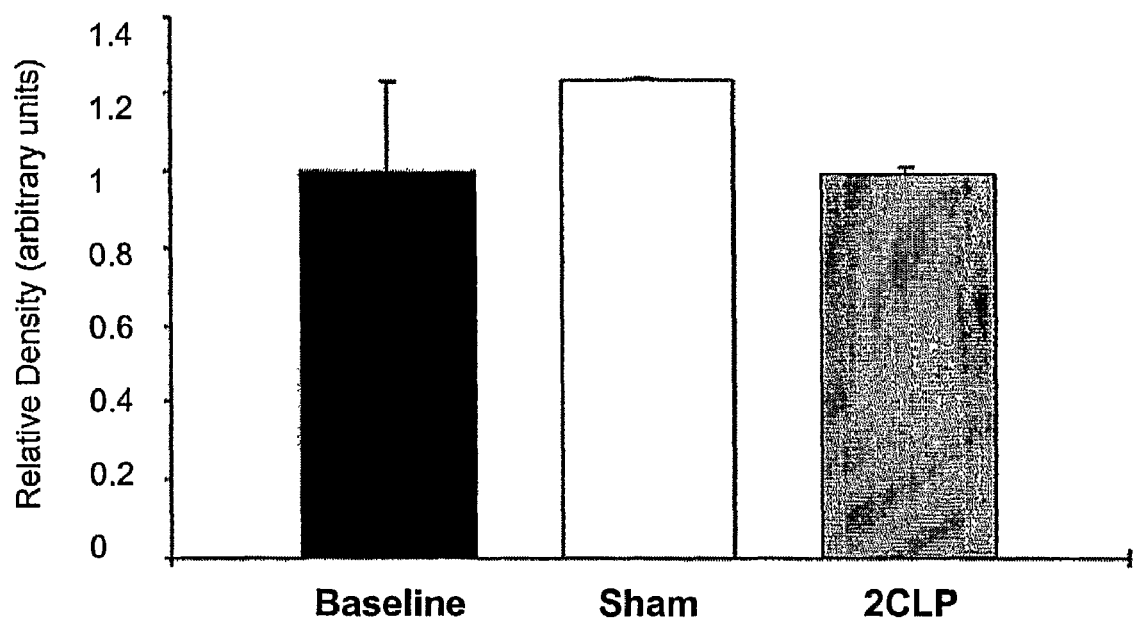

Myocardial Glycogen Deposition:

Histologic analysis demonstrated increased periodic acid-Schiff-positive glycogen deposits in the perinuclear region and between myocytes following 2CLP compared with sham-operated and nonoperated mice (FIG. 16E).

Arterial Oxygen Tension and Myocardial Perfusion:

Measurement of Pao$_2$ during spontaneous ventilation of room air revealed little difference between nonoperated, sham-operated, and septic mice (93.5±9.2 vs. 99.7±29.6 and 94.7±16.7 mmHg, respectively, p not significant). Heart lung ratios of (99m)Tc sestamibi, although slightly increased following sham operation, were not statistically different between groups (FIG. 17).

Discussion

The results of this study demonstrate that the changes seen during myocardial hibernation occur in the septic heart. These results may have dramatic implications. Although hibernation is an adaptive mechanism for cardiomyocytes to maintain viability during hypoxia, our findings represent the first demonstration of hibernation in a non-ischemic disease state.

Ventricular dysfunction is a requisite feature of hibernation. In this study, septic mice demonstrated cardiac dysfunction as evidenced by decreased cardiac output and stroke volume. These results support previous work with this well-validated model that demonstrated decreased cardiac performance 24 hrs post-2CLP and progressively decreased contractility beginning 6 hrs post-2CLP (Yang S et al., Shock 2002; 17:55-60 and Tao W et al., Shock 2004; 21:31-37).

The results reported here also strengthen the proposal that cytopathic hypoxia underlies cardiac dysfunction in sepsis. This provides an explanation for important observations regarding cardiac ATP abundance in sepsis. Specifically, one of the arguments against the validity of the cytopathic hypoxia hypothesis has been that ATP content in the dysfunctional heart is preserved in sepsis (Solomon M A et al., Am J Physiol 1994; 266:H757-H768 and Hotchkiss R S et al., Am J Physiol 1991; 260:C50-C57). However, maintenance of ATP levels would be expected if septic myocardium hibernates in response to a block in oxidative phosphorylation, substantially reducing ATP demand (Budinger G R et al., J Biol Chem 1998; 273:3320-3326).

Further support for the concept of cellular dysoxia during sepsis is provided by the observed increase in myocardial glucose utilization. During ischemia and hypoxia, the absence of oxygen at the cellular level leads to increased myocardial glucose uptake to facilitate anaerobic glycolysis (Nishino Y et al., Cardiovascular Res 2004; 61:610-619). In contrast, during sepsis, tissue oxygen is often abundant and readily available for aerobic ATP production, and myocardial perfusion is preserved or even increased. Using a 2CLP model, Hotchkiss and colleagues (Hotchkiss R S et al., Am J Physiol regul Integr Comp Physiol 1991; 261:965-972) demonstrated that tissue hypoxia does not occur in the heart or other organs during sepsis and that arterial oxygen tension and organ perfusion are maintained. The key in sepsis is not oxygen availability but oxygen utilization. A sepsis-induced irreversible inhibition of cytochrome oxidase has been previously demonstrated. Coupling this finding with data indicating an increase in myocardial glycolysis clearly indicates that the cellular environment in sepsis becomes "functionally hypoxic" despite the presence of oxygen. This provides strong support for the concept that cytopathic hypoxia underlies impaired oxygen utilization in sepsis. These results, along with those using azide to induce cellular hypoxia, suggest that cytochrome oxidase is the sensor that initiates myocardial hibernation.

Finally, inhibition of cytochrome oxidase might be involved in sepsis-associated dysfunction in organs other than the heart. Sepsis is characterized by functional abnormalities in lung, liver, vasculature, kidney, central nervous, and immune systems, among others. Remarkably, in none of these has a characteristic pathologic abnormality been identified. Furthermore, the etiology of dysfunction in each organ system, as well as a global cause of death, remains obscure. It may be postulated that the organ-system dysfunction of sepsis and related inflammatory states represents multiple organ hibernation. Hibernation, although adaptive and potentially protective during ischemia and hypoxia, may be pathologic during sepsis and, if persistent, may ultimately result in death. Certainly, the demonstration that cytochrome oxidase inhibition eventually becomes irreversible is consistent with this hypothesis.

As mentioned previously, there are certain instances where it may desirable to induce stasis or hibernation in a biological material (e.g., a cell or tissue) or a patient. See for example, US Patent Application 20050135125 to Mark B. Roth. Based on the results disclosed herein, cytochrome c therapy can overcome any etiology of cytochrome oxidase inhibition whether it be related to sepsis, trauma, or intentionally induced as disclosed by Roth. Thus, in accordance with the present invention, methods of administration of cytochrome c to such patients or biological material are provided which reverse the induced state of hibernation or stasis, thereby restoring cell and/or organ function.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for the treatment of sepsis and/or sepsis-associated cardiac dysfunction in a patient in need thereof comprising administration of an effective amount of cytochrome c to said patient.

2. The method of claim 1, wherein said cytochrome c is administered intravenously.

3. The method of claim 1, further comprising administration of an amount of ascorbic acid effective to reduce said cytochrome c.

4. The method of claim 1, wherein said method is for the treatment of sepsis associated with a condition selected from the group consisting of systemic inflammatory response syndrome, (SIRS), and multiple organ dysfunction syndrome (MODS).

5. The of claim 1 wherein said cardiac dysfunction is associated with a condition selected from the group consisting of burns, trauma, hemorrhage, cardiopulmonary bypass, hypoxia and ischemia, cardiomyopathies, smoke inhalation, carbon monoxide poisoning, inborn errors of metabolism, mitochondriopathies, and induction of stasis or hibernation.

6. The method of claim 3, wherein said cytochrome C is reduced prior to administration.

7. The method of claim 1, wherein said cytochrome c is in reduced form.

8. The method of claim 7, wherein the reduced cytochrome c is ferrocytochrome c.

9. A method for identifying agents having efficacy in the treatment of sepsis-associated cardiac dysfunction comprising
    a) providing a septic subject, said sepsis being caused by a cecal ligation and pucture procedure,
    b) administering a test agent to said subject, and
    c) determining whether said agent improves cardiac function in said septic subject, said improvement comprising restoration of oxidative capacity.

10. The method of claim 9, wherein said restoration of oxidative capacity comprises a process selected from the group consisting of at least one of a decrease in myocardial glucose uptake, a decrease in steady-state levels of myocardial GLUT4, and a decrease in glycogen deposition.

* * * * *